(12) United States Patent
Ye et al.

(10) Patent No.: US 11,585,953 B2
(45) Date of Patent: Feb. 21, 2023

(54) SYSTEMS FOR IMAGING

(71) Applicant: SHANGHAI UNITED IMAGING HEALTHCARE CO., LTD., Shanghai (CN)

(72) Inventors: Ting Ye, Wuhan (CN); Yajun Wu, Shanghai (CN)

(73) Assignee: SHANGHAI UNITED IMAGING HEALTHCARE CO., LTD., Shanghai (CN)

(*) Notice: Subject to any disclaimer, the term of this patent is extended or adjusted under 35 U.S.C. 154(b) by 30 days.

(21) Appl. No.: 17/216,917

(22) Filed: Mar. 30, 2021

(65) Prior Publication Data

US 2021/0215838 A1 Jul. 15, 2021

Related U.S. Application Data

(63) Continuation of application No. PCT/CN2019/109667, filed on Sep. 30, 2019.

(30) Foreign Application Priority Data

Sep. 30, 2018 (CN) .......................... 201811161257.X
Dec. 12, 2018 (CN) .......................... 201811516847.X

(51) Int. Cl.
*G01N 23/046* (2018.01)
*G01T 7/00* (2006.01)
*G01T 1/161* (2006.01)

(52) U.S. Cl.
CPC ............. *G01T 7/00* (2013.01); *G01N 23/046* (2013.01); *G01N 2223/3103* (2013.01); *G01T 1/161* (2013.01)

(58) Field of Classification Search
CPC ........ G01T 7/00; G01T 1/161; G01T 1/2018; G01N 23/046; G01N 2223/3103;
(Continued)

(56) References Cited

U.S. PATENT DOCUMENTS

| 5,610,968 A | 3/1997 | Deucher et al. |
| 2005/0117698 A1* | 6/2005 | Lacey .................... A61B 6/035 378/19 |

(Continued)

FOREIGN PATENT DOCUMENTS

| CN | 105455836 A | 4/2016 |
| CN | 105530751 A | 4/2016 |

(Continued)

OTHER PUBLICATIONS

International Search Report in PCT/CN2019/109667 dated Dec. 27, 2019, 5 pages.

(Continued)

*Primary Examiner* — Kiho Kim
(74) *Attorney, Agent, or Firm* — Metis IP LLC

(57) ABSTRACT

The present disclosure may provide a detector module of an imaging apparatus. The detector module may include a detector assembly configured to detect a signal associated with an object; a cover assembly configured to accommodate the detector assembly; and at least one cooling assembly operably coupled to the cover assembly. The at least one cooling assembly may be configured to cool the detector assembly by providing a cooling medium to the cover assembly.

20 Claims, 19 Drawing Sheets

(58) Field of Classification Search
CPC ......... A61B 6/4488; A61B 6/037; A61B 6/42; A61B 6/03
See application file for complete search history.

(56) References Cited

U.S. PATENT DOCUMENTS

| | | |
|---|---|---|
| 2006/0037739 A1 | 2/2006 | Utsunomiya |
| 2007/0284535 A1* | 12/2007 | Heismann ............... A61B 6/035 250/370.15 |
| 2010/0188082 A1 | 7/2010 | Morich et al. |
| 2013/0134313 A1 | 5/2013 | Öhner et al. |
| 2017/0059720 A1* | 3/2017 | McBroom ............. G01T 1/2985 |
| 2018/0275293 A1 | 9/2018 | Hefetz et al. |
| 2019/0331810 A1 | 10/2019 | Yan et al. |

FOREIGN PATENT DOCUMENTS

| | | |
|---|---|---|
| CN | 106659064 A | 5/2017 |
| CN | 106765788 A | 5/2017 |
| CN | 106901772 A | 6/2017 |
| CN | 106923857 A | 7/2017 |
| CN | 107027274 A | 8/2017 |
| CN | 107510469 A | 12/2017 |
| CN | 206777337 U | 12/2017 |
| CN | 207196684 U | 4/2018 |
| CN | 107981881 A | 5/2018 |
| CN | 107997779 A | 5/2018 |
| CN | 207652878 U | 7/2018 |
| CN | 108420447 A | 8/2018 |
| CN | 109152299 A | 1/2019 |
| CN | 109480885 A | 3/2019 |
| JP | 2001153959 A * | 6/2001 |

OTHER PUBLICATIONS

Written Opinion in PCT/CN2019/109667 dated Dec. 27, 2019, 5 pages.
First Office Action in Chinese Application No. 201811161257.X dated Sep. 3, 2019, 15 pages.
First Office Action in Chinese Application No. 201811516847.X dated Feb. 3, 2020, 23 pages.

* cited by examiner

1400

142

SYSTEMS FOR IMAGING

CROSS-REFERENCE TO RELATED APPLICATIONS

This application is a Continuation of International Application No. PCT/CN2019/109667, filed on Sep. 30, 2019, which claims priority of Chinese Patent Application No. 201811161257.X filed on Sep. 30, 2018 and Chinese Patent Application No. 201811516847.X filed on Dec. 12, 2018, the contents of each of which are hereby incorporated by reference in its entirety.

TECHNICAL FIELD

The present disclosure generally relates to an imaging apparatus, and more specifically relates to a detector module of the imaging apparatus.

BACKGROUND

In the medical imaging field, an imaging system, e.g., a positron emission tomography (PET) system, a tomography-computed tomography (CT) system, is used to acquire imaging data and reconstruct one or more images showing the anatomy and/or a physiological process of an object in either health or disease state. For illustration purposes, the CT system includes an X-ray tube and a detector module. The X-ray tube emits X rays towards the object. The detector module receives attenuated X rays passing through the object and detects and/or processes signal(s) (e.g., electrical signal(s)) thereof. Further, the signal(s) are further used to reconstruct the image(s). Usually, the detector module generates a large amount of heat, e.g., during receiving the attenuated X rays, detecting and/or processing the signal(s) thereof. If the heat is accumulated to a certain extent, the detector module fails to function properly and the signal(s) are inaccurate, thereby affecting the accuracy of the image(s) reconstructed based on the inaccurate signal(s).

Besides, the detector module usually includes a plurality of detector components arranged in rows and/or columns, so that the detector module has a certain width and/or length to efficiently receive the X rays passing through the object. One or more detector components located at a central region of the detector module generate more heat than one or more detector components close to the end(s) of the detector module. Additionally, heat dissipation in the detector module is relatively slow because of a limited heat exchange coefficient of the material of the detector module. Therefore, in comparison with the detector components close to the end(s) of the detector module, the heat generated at the central region of the detector module slowly or merely dissipates, thereby causing overheating and/or a temperature gradient in different positions of the detector module. For illustration purposes, the detector components at the central region of the detector module may have higher temperatures than those close to the end(s) of the detector module. Accordingly, the responses of the plurality of detector components are inconsistent and the signal(s) are inaccurate, thereby affecting the accuracy of the reconstructed image(s). Besides, the heat also affects the service life, the stability and/or work efficiency of the detector module.

To solve the problems, current ways include cooling the detector module by providing a cooling medium (e.g., a cooling gas). For illustration purposes, the detector module may include one or more fans located at one or more sides of the detector module, which allows the cooling gas to flow between different sides of the detector module and cool the detector module. However, the cooling efficiency of the fan(s) is limited because of a limited size of the fan(s), so that only using the fan(s) to allow the cooling gas to flow between different sides of the detector module is insufficiently to efficiently solve the problem of overheating and/or the temperature gradient. Besides, in some cases, the gas inside the detector module is in fluid communication with the gas outside the detector module, thus it is also time-consuming to cool the detector module. Thus, it is desirable to provide a detector module that can be evenly and quickly cooled, thereby ensuring the accuracy of signal(s) associated with an object detected and/or processed by the detector module and the quality of image(s) reconstructed based on the signal(s).

SUMMARY

In one aspect of the present disclosure, a detector module may be provided. The detector module may include a detector assembly configured to detect a signal associated with an object; a cover assembly configured to accommodate the detector assembly; and at least one cooling assembly operably coupled to the cover assembly. The at least one cooling assembly may be configured to cool the detector assembly by providing a cooling medium to the cover assembly.

In some embodiments, the cooling medium may include a gas.

In some embodiments, the cover assembly may include at least one first gas inlet and at least one first gas outlet. Each of the at least one cooling assembly may include a second gas inlet and a second gas outlet. The at least one first gas inlet and the at least one first gas outlet of the cover assembly, and the second gas inlet and the second gas outlet of the each of the at least one cooling assembly may be configured to form a fluid communication between the cover assembly and the at least one cooling assembly.

In some embodiments, the second gas inlet is operably coupled to one of the at least one first gas outlet. The second gas outlet may be operably coupled to one of the at least one first gas inlet.

In some embodiments, each of the at least one first gas inlet and a corresponding first gas outlet of the at least one first gas outlet may be arranged along a width direction of the cover assembly.

In some embodiments, the second gas outlet and the second gas inlet may be arranged at a cover of the at least one cooling assembly.

In some embodiments, the detector module may further comprise a first connection passage and a second connection passage located between the cover assembly and the at least one cooling assembly. The second gas inlet may be operably coupled to one of the at least one first gas outlet through the second connection passage. The second gas outlet may be operably coupled to one of the at least one first gas inlet through the first connection passage.

In some embodiments, the detector module may further comprise a gas inlet chamber located inside the cover assembly. The gas inlet chamber may be in fluid communication with the at least one first gas inlet.

In some embodiments, the gas inlet chamber may include a sidewall configured to allow the gas to flow into the detector assembly.

In some embodiments, the sidewall of the gas inlet chamber may include one or more holes.

In some embodiments, the gas inlet chamber may be arranged along a length direction of the cover assembly.

In some embodiments, the detector module may further comprise a gas outlet chamber located inside the cover assembly. The gas outlet chamber may be in fluid communication with the at least one first gas outlet.

In some embodiments, the gas outlet chamber may include a sidewall configured to allow the gas to flow out of the detector assembly.

In some embodiments, the sidewall of the gas outlet chamber may include one or more holes.

In some embodiments, the gas outlet chamber may be arranged along a length direction of the cover assembly.

In some embodiments, the at least one cooling assembly may include a refrigeration circuit.

In some embodiments, the refrigeration circuit may include an evaporator located inside the at least one cooling assembly. The evaporator may be configured to cool the gas flowing between the cover assembly and the at least one cooling assembly.

In some embodiments, the refrigeration circuit may further include a condenser and a compressor.

In some embodiments, the at least one cooling assembly may further include a thermoelectric cooler (TEC).

In some embodiments, the thermoelectric cooler may include a cold side located inside the at least one cooling assembly. The cold side may be configured to cool the gas flowing between the cover assembly and the at least one cooling assembly.

In some embodiments, the at least one cooling assembly may further include at least one fan located inside the at least one cooling assembly, and the at least one fan may be configured to regulate or accelerate a flow rate of the gas flowing between the cover assembly and the at least one cooling assembly.

In some embodiments, the at least one fan may include a first fan and a second fan, and the first fan may be located near one of the at least one first gas inlet, and the second fan may be located near one of the at least one first gas outlet.

In some embodiments, the cover assembly may include: a support component configured to support the detector assembly; and a shell operably coupled to the support component. The support component and the shell may form a chamber to accommodate the detector assembly.

In some embodiments, the cooling medium may include a liquid.

In some embodiments, the at least one cooling assembly may include a plurality of pipes arranged in the detector assembly; and a medium separation component operably coupled to the plurality of pipes and configured to distribute the cooling medium into the plurality of pipes to cool the detector assembly.

In another aspect of the present disclosure, a detector module may be provided. The detector module may include: a support component configured to support a detector assembly of the detector module; a shell operably coupled to the support component, the support component and the shell forming a chamber to accommodate the detector assembly; and at least one cooling assembly configured to cool a gas flowing between the shell and a cover of the at least one cooling assembly. The shell may include at least one first gas inlet and at least one first gas outlet configured to guide the gas to cool the detector assembly. The cover of the at least one cooling assembly may include at least one second gas inlet and at least one second gas outlet. One of the at least one second gas inlet may be operably coupled to a corresponding first gas outlet of the at least one first gas outlet. One of the at least one second gas outlet may be operably coupled to a corresponding first gas inlet of the at least one first gas inlet.

In another aspect of the present disclosure, a detector module may be provided. The detector module may include: a cover assembly including a chamber; a detector assembly including a plurality of detector components arranged inside the chamber; a plurality of pipes arranged in the plurality of detector components, respectively; and a medium separation component operably coupled to the plurality of pipes. The medium separation component may be configured to distribute a cooling medium into the plurality of pipes. Each of the plurality of pipes may be configured to guide a portion of the cooling medium to flow through a corresponding detector component of the plurality of detector components and cool the corresponding detector component.

In some embodiments, the medium separation component may include one or more medium separation sub-components. Each of the one or more medium separation sub-components may be operably coupled to at least a portion of the plurality of pipes; and the each of the one or more medium separation sub-components may be configured to distribute a portion of the cooling medium to the one or more pipes of the plurality of pipes.

In some embodiments, the each of the one or more medium separation sub-components may include a main medium inlet, a main medium outlet, one or more branch medium inlets, and one or more branch medium outlets; and the cooling medium may be capable of flowing from the main medium inlet to the one or more branch medium outlets or from the one or more branch medium inlets to the main medium outlet.

In some embodiments, the each of the plurality of pipes may include an inlet port and an outlet port. Each of the one or more branch medium outlets may be operably coupled to an inlet port of one of the plurality of pipes; and each of the one or more branch medium inlets may be operably coupled to an outlet port of one of the plurality of pipes.

In some embodiments, the each of the one or more medium separation sub-components may include a medium separation plate; and the main medium inlet, the main medium outlet, the one or more branch medium inlets and the one or more branch medium outlets may be arranged at the medium separation plate.

In some embodiments, inlet ports of the at least a portion of the plurality of pipes and outlet ports of the at least a portion of the plurality of pipes may be arranged at a same side facing the medium separation plate.

In some embodiments, the each of the one or more medium separation sub-components may include a first medium separation plate and a second medium separation plate; the main medium inlet and the one or more branch medium outlets may be arranged at the first medium separation plate; and the main medium outlet and the one or more branch medium inlets may be arranged at the second medium separation plate.

In some embodiments, inlet ports of the at least a portion of the plurality of pipes and outlet ports of the at least a portion of the plurality of pipes may be arranged at two sides such that the inlet ports are facing the first medium separation plate, and the outlet ports are facing the second medium separation plate, respectively.

In some embodiments, at least one of the one or more medium separation sub-components may be operably coupled to one or more detector components of the plurality of detector components that are located at a central region of the detector assembly.

In some embodiments, the medium separation component may include at least one flow regulating component; and the at least one flow regulating component may be configured to regulate at least one flow rate of the cooling medium flowing through the at least a portion of the plurality of pipes.

In some embodiments, at least one of the one or more medium separation sub-components may be equipped with one of the at least one flow regulating component.

In some embodiments, an average flow rate of the cooling medium flowing through one or more pipes coupled to the at least one of the one or more medium separation sub-components may be greater than or equal to an average flow rate of the cooling medium flowing through one or more pipes coupled to a remaining portion of the one or more medium separation sub-components.

In some embodiments, a first count of the one or more branch medium inlets or a first count of the one or more branch medium outlets of a first medium separation sub-component of the one or more medium separation sub-components may be different from a second count of the one or more branch medium inlets or a second count of the one or more branch medium outlets of a second medium separation sub-component of the one or more medium separation sub-components.

In some embodiments, a first count of the one or more branch medium inlets or a first count of the one or more branch medium outlets of the at least one of the one or more medium separation sub-components may be smaller than or equal to a second count of the one or more branch medium inlets or a second count of the one or more branch medium outlets of each of the remaining portion of the one or more medium separation sub-components.

In some embodiments, a first branch medium outlet of the one or more branch medium outlets of the each of the one or more medium separation sub-components may be closer to the main medium inlet of the each of the one or more medium separation sub-components than a second branch medium outlet of the one or more branch medium outlets; and a first opening size of the first branch medium outlet may be less than or equal to a second opening size of the second branch medium outlet.

In some embodiments, at least one of the one or more medium separation sub-components may include a chamber configured to store the cooling medium.

In some embodiments, the medium separation component may include a first medium separation sub-component, a second medium separation sub-component, and a third medium separation sub-component; and the first medium separation sub-component, the second medium separation sub-component, and the third medium separation sub-component may be independent from each other and disconnected with each other.

In some embodiments, each of the plurality of detector components may include: an electronic component; and a frame for supporting the electronic component. The frame may be equipped with a pipe of the plurality of pipes.

In some embodiments, the pipe may be located at a central region of the frame.

In some embodiments, the pipe may extend along a length direction of the frame or a length direction of the electronic component.

In some embodiments, an inlet port of the pipe and an outlet port of the pipe may be located at different positions along a height direction of the frame or a height direction of the electronic component.

In some embodiments, the inlet port of the pipe may be located closer to the electronic component than the outlet port of the pipe in the height direction of the frame.

In some embodiments, the frame may include a groove, and the pipe may be mounted in the groove.

In some embodiments, the pipe may be mounted in the groove by welding, embedding, pasting, or through a mechanical fastener.

In some embodiments, a surface of the frame and a surface of the pipe may form a coplane.

In some embodiments, the detector module may further comprise at least one cooling assembly operably coupled to the cover assembly. The at least one cooling assembly may be configured to cool the detector assembly by providing a cooling gas to the cover assembly.

In some embodiments, each two adjacent detector components of the plurality of detector components may include a gap between the each two adjacent detector components; and the at least one cooling assembly may be configured to cool the detector assembly by providing a cooling gas to the gap between each two adjacent detector components.

In another aspect of the present disclosure, a detector module may be provided. The detector module may include: a cover assembly including a chamber; a plurality of detector components arranged inside the chamber; a plurality of pipes arranged in the plurality of detector components, respectively, and configured to provide a plurality of passages for a cooling medium; a medium separation component including one or more medium separation sub-components independent from each other and disconnected with each other. Each of the one or more medium separation sub-components may be operably coupled to at least a portion of the plurality of pipes; and each of the one or more medium separation sub-components may include a main medium inlet, a main medium outlet, one or more branch medium inlets, and one or more branch medium outlets; and each of the one or more branch medium outlets may be operably coupled to an inlet port of one of the plurality of pipes; and each of the one or more branch medium inlets may be operably coupled to an outlet port of one of the plurality of pipes.

In another aspect of the present disclosure, an imaging apparatus may be provided. The imaging apparatus may include: a frame assembly; a tube mounted on the frame assembly and configured to emit radiation rays; and a detector module mounted on the frame assembly and configured to detect at least a portion of the radiation rays. The detector module may include: a cover assembly including a chamber; a detector assembly including a plurality of detector components arranged inside the chamber; a plurality of pipes arranged in the plurality of detector components, respectively; and a medium separation component operably coupled to the plurality of pipes. The medium separation component may be configured to distribute a cooling medium into the plurality of pipes, and each of the plurality of pipes may be configured to guide a portion of the cooling medium to flow through a corresponding detector component of the plurality of detector components and cool the corresponding detector component.

In another aspect of the present disclosure, a detector module may be provided. The detector module may include: a detector assembly configured to detect a signal associated with an object; a cover assembly configured to accommodate the detector assembly; a plurality of cooling pipes arranged in the cover assembly; and at least one medium separation component operably coupled to the plurality of cooling pipes. The at least one medium separation component may be configured to distribute a cooling medium into the plurality of cooling pipes.

In some embodiments, the detector module may further include a plurality of connection pipes. The plurality of connection pipes may be operably coupled to the at least one medium separation component and the plurality of cooling pipes; and the plurality of connection pipes may be configured to allow the cooling medium to flow between the plurality of cooling pipes and the medium separation component.

In some embodiments, the plurality of connection pipes may include one or more inlet connection pipes and one or more outlet connection pipes; and the cooling medium may be capable of flowing from the at least one medium separation component, through the one or more inlet connection pipes, to the plurality of cooling pipes or from the plurality of cooling pipes, through the one or more outlet connection pipes, to the at least one medium separation component.

In some embodiments, each of the at least one medium separation component may include a main medium inlet, a main medium outlet, one or more branch medium inlets, and one or more branch medium outlets. The one or more inlet connection components may be operably coupled to the one or more branch medium outlets. The one or more outlet connection components may be operably coupled to the one or more branch medium inlets; and the cooling medium may be capable of flowing from the main medium inlet, through the one or more branch medium outlets, into the one or more inlet connection pipes or from the one or more outlet connection pipes, through the one or more branch medium inlets, into the main medium outlet.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
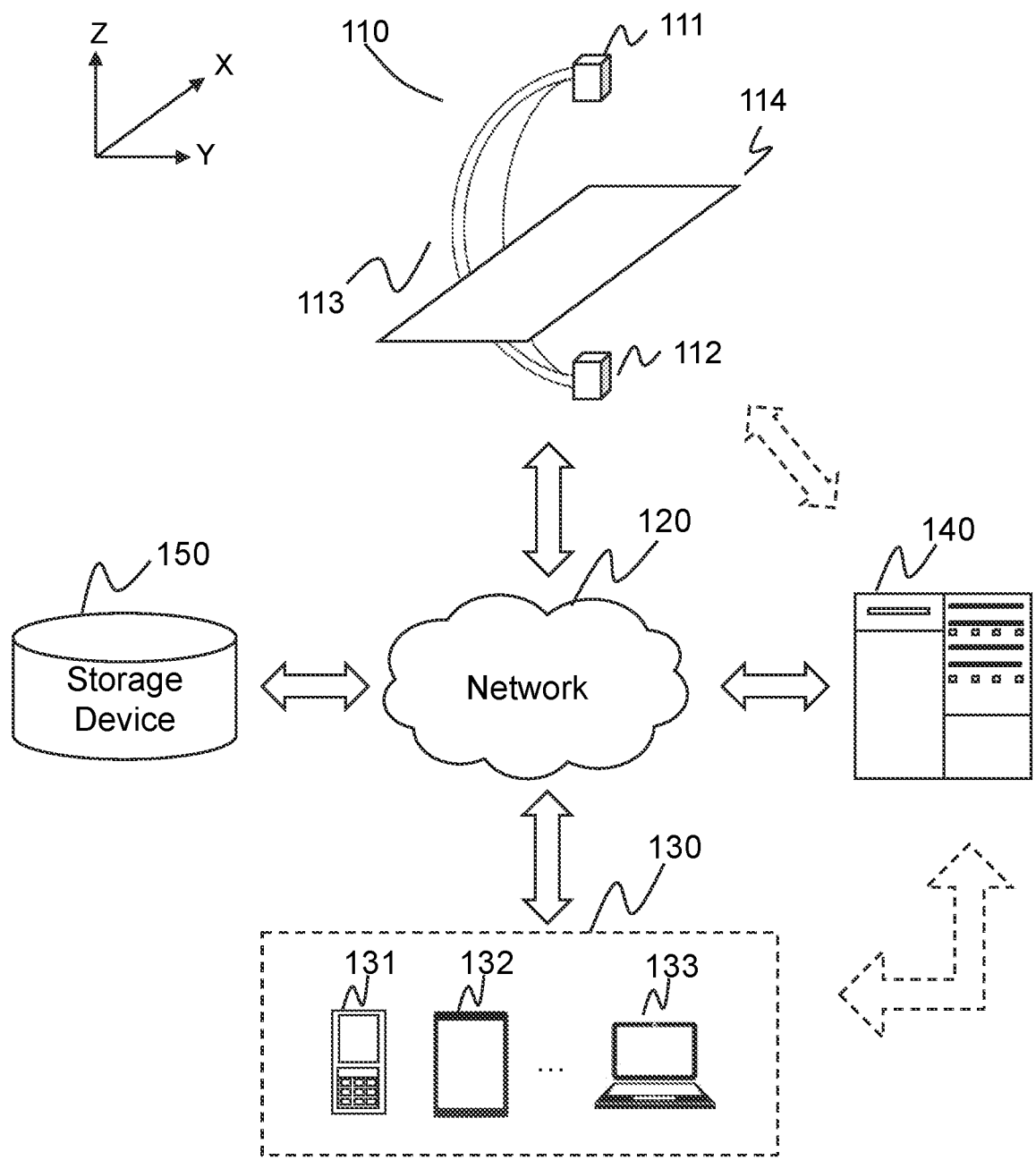
FIG. 1 is a schematic diagram illustrating an exemplary imaging system according to some embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be further understood that the terms "cover," "base," "hole," "component," "assembly," etc., when used in this disclosure, refer to one or more parts with one or more specific purposes. However, a structure that may perform a same or similar function compared to a part exemplified above or referred to elsewhere in the present disclosure may be named differently from the present disclosure.

The terminology used herein is to describe particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "unit," "module," and/or "block" used herein are one method to distinguish different components, elements, parts, section or assembly of different level in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

It will be understood that, although the terms "first," "second," "third," etc., may be used herein to describe various elements, these elements should not be limited by these terms. These terms are only used to distinguish one element from another. For example, a first element could be termed a second element, and, similarly, a second element could be termed a first element, without departing from the scope of exemplary embodiments of the present disclosure.

Spatial and functional relationships between elements are described using various terms, including "connected," "attached," and "mounted." Unless explicitly described as being "direct," when a relationship between first and second elements is described in the present disclosure, that relationship includes a direct relationship where no other intervening elements are present between the first and second elements, and also an indirect relationship where one or more intervening elements are present (either spatially or functionally) between the first and second elements. In contrast, when an element is referred to as being "directly" connected, attached, or positioned to another element, there are no intervening elements present. Other words used to describe the relationship between elements should be interpreted in a like fashion (e.g., "between," versus "directly between," "adjacent," versus "directly adjacent," etc.).

It should also be understood that terms such as "top," "bottom," "upper," "lower," "vertical," "lateral," "above," "below," "upward(s)," "downward(s)," "left-hand side," "right-hand side," "left," "right," "horizontal," and other such spatial reference terms are used in a relative sense to describe the positions or orientations of certain surfaces/parts/components of the imaging device with respect to other such features of the imaging device when the imaging device is in a normal operating position and may change if the position or orientation of the imaging device changes.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The present disclosure relates to a detector module. In some embodiments, the detector module may include a detector assembly, a cover assembly, and at least one cooling assembly. The detector assembly may be configured to detect signal(s) associated with an object. The cover assembly may be configured to accommodate the detector assembly. The at least one cooling assembly may be operably coupled to the cover assembly. The at least one cooling assembly may be configured to cool the detector assembly by providing a cooling medium (e.g., a gas, a liquid) to the cover assembly. Specifically, the cooling medium may flow into the cover assembly to absorb heat generated by the detector assembly. The heat-laden cooling medium may flow back to the cooling assembly to be cooled for reuse. This process may be repeated to cool the detector assembly. In some embodiments, the cover assembly and the cooling assembly may have or form sealed structures so that the gas inside the cover assembly and the cooling assembly may not exchange with the gas outside the detector module, and the gas flowing between the cover assembly and the cooling assembly may have a relatively low temperature. The temperature of the gas inside the cover assembly and the cooling assembly may quickly decrease to an acceptable temperature level to cool the detector assembly. In some embodiments, a gas inlet chamber and a gas outlet chamber may be disposed at two sides of the detector assembly along a length direction of the detector assembly. The cooling medium may pass the detector assembly through the gas inlet chamber and the heat-laden cooling medium may flow out of the detector assembly into the gas outlet chamber. Further, the heat-laden cooling medium may flow back to the cooling assembly to be cooled for reuse. Therefore, the cooling medium may simultaneously (almost simultaneously) absorb heat generated by each of a plurality of detector components included in the detector assembly, thereby evenly cooling the plurality of detector components, and avoiding (or reducing, or eliminating) a temperature gradient in different positions of the detector assembly.

In some embodiments, the detector module may include a detector assembly, a cover assembly, a plurality of pipes, and a medium separation component. The detector assembly may be configured to detect signal(s) associated with an object. The cover assembly may include a chamber configured to accommodate the detector assembly. The detector assembly may include a plurality of detector components arranged inside the chamber. The medium separation component may be operably coupled to the plurality of pipes. The medium separation component may be configured to distribute a cooling medium into the plurality of pipes. Each of the plurality of pipes may be configured to guide a portion of the cooling medium to flow through a corresponding detector component of the plurality of detector components and cool the corresponding detector component. In some embodiments, the plurality of pipes may be independent from each other and disconnected with each other. Each of the plurality of detector components may be cooled by the cooling medium flowing in the corresponding pipe. Specifically, the cooling medium may simultaneously (almost simultaneously) absorb heat generated by each of the plurality of detector components, thereby evenly cooling the plurality of detector components, and avoiding (or reducing, or eliminating) a temperature gradient in different positions of the detector assembly.

It should be noted the above descriptions of the detector module may be provided for illustration purposes and not limit the scope of the present disclosure. In some embodiments, the detector module may include the detector assembly, the cover assembly, the at least one cooling assembly, the plurality of pipes, and the medium separation component as illustrated above.

FIG. 1 is a schematic diagram illustrating an exemplary imaging system 100 according to some embodiments of the present disclosure. The imaging system 100 may generate an image of an object. The object may include a biological object and/or a non-biological object. The biological object may be a human being, an animal, a plant, or a portion thereof (e.g., cell, tissue, organ). In some embodiments, the object may be a man-made composition of organic and/or inorganic matters that are with or without life. In the present disclosure, "object" and "subject" are used interchangeably. As illustrated, the imaging system 100 may include a scanner 110, a network 120, a terminal 130, a processing device 140, and a storage device 150. The components of the imaging system 100 may be connected in one or more of various ways. Mere by way of example, as illustrated in FIG. 1, the scanner 110 may be connected to the processing device 140 through the network 120. As another example, the scanner 110 may be connected to the processing device 140 directly as indicated by the bi-directional arrow in dotted lines linking the scanner 110 and the processing device 140. As a further example, the storage device 150 may be connected to the processing device 140 directly or through the network 120. As still a further example, a terminal (e.g., 131, 132, 133, etc.) may be connected to the processing device 140 directly (as indicated by the bi-directional arrow in dotted lines linking the terminal 130 and the processing device 140) or through the network 120.

The scanner 110 may scan an object, and generate data relating to the object. In some embodiments, the scanner 110 may be a medical imaging device, for example, a PET apparatus, a SPECT apparatus, a CT apparatus, or the like, or any combination thereof (e.g., a PET-CT apparatus, a PET-MRI apparatus, or a SPECT-MRI apparatus). Taking a CT apparatus as an example, the scanner 110 may include a tube (e.g., an X-ray tube) 111, a detector module 112, a frame assembly 113, and a table 114. The table 114 may be configured to support the object.

In some embodiments, the frame assembly 113 may be configured to support one or more components of the scanner 110. For example, the tube 111 and the detector module 112 may be mounted on the frame assembly 113. The frame assembly 113 may be arc-shaped (e.g., a C-shaped arm, a G-shaped arm, etc.), ring-shaped, etc. In some embodiments, the frame assembly 113 may include a rotary frame and a fixed frame. The fixed frame may be configured to support one or more parts (e.g., the tube 111, the detector module 112, the rotary frame) of the scanner 110. The rotary frame may be rotatably coupled to the fixed frame. The rotary frame may be configured to rotate along e.g., a guide rail mounted on the fixed frame. In some embodiments, the tube 111 and the detector module 112 may be mounted symmetrically on the rotary frame. For example, the tube 111 may be mounted opposite to a central region of the detector module 112. That is, the tube 111, a rotation center of the rotary frame, and a center of the central region of the detector module 112 may be disposed on a same line.

The tube 111 may be configured to emit radiation rays (e.g., X rays) towards an object (e.g., a patient). The detector module 112 may be configured to receive attenuated X rays passing through the object. The detector module 112 may also be configured to detect signal(s) associated with the object. The detector module 112 may also process the signal(s) and/or transmit the processed signal(s) to other components (e.g., an image reconstruction component of the CT apparatus) of the imaging system 100 for image reconstruction. The reconstructed image may be used for medical diagnosis, e.g., by a doctor. In some embodiments, the detector module 112 may include a scintillation detector (e.g., a cesium iodide detector), a gas detector, etc. In some embodiments, the detector module 112 may include a circular detector, a square detector, an arcuate detector, or the like, or any combination thereof.

In some embodiments, the detector module 112 may include a detector assembly, a cover assembly, and at least one cooling assembly. The detector assembly may be configured to detect the signal(s) associated with an object. The cover assembly may be configured to accommodate the detector assembly. The at least one cooling assembly may be operably coupled to the cover assembly. The at least one cooling assembly may be configured to cool the detector assembly by providing a cooling medium (e.g., a gas, a liquid) to the cover assembly. Specifically, the cooling medium may flow into the cover assembly to absorb heat generated by the detector assembly. The heat-laden cooling medium may flow back to the cooling assembly to be cooled for reuse. This process may be repeated to cool the detector assembly. In some embodiments, the cover assembly and the cooling assembly may have or form sealed structures so that the gas inside the cover assembly and the cooling assembly may not exchange with the gas outside the detector module 112. The temperature of the gas inside the cover assembly and the cooling assembly may quickly decrease to an acceptable temperature level to cool the detector assembly. In some embodiments, a gas inlet chamber and a gas outlet chamber may be disposed at two sides of the detector assembly along a length direction of the detector assembly. The cooling medium may pass the detector assembly through the gas inlet chamber, absorb heat from the detector assembly, and the heat-laden cooling medium may flow out of the detector assembly into the gas outlet chamber. Further, the heat-laden cooling medium may flow back to the cooling assembly to be cooled for reuse. Therefore, the cooling medium may simultaneously (almost simultaneously) absorb heat generated by each of a plurality of detector components included in the detector assembly, thereby evenly cooling the plurality of detector components, and avoiding (or reducing, or eliminating) a temperature gradient in different positions of the detector assembly.

In some embodiments, the at least one cooling assembly may include a medium separation component. The medium separation component may be operably coupled to a plurality of pipes located at the detector assembly. The medium separation component may be configured to distribute a cooling medium into the plurality of pipes. Each of the plurality of pipes may be configured to guide a portion of the cooling medium to flow through a corresponding detector component of the plurality of detector components and cool the corresponding detector component. In some embodiments, the plurality of pipes may be independent from each other and disconnected with each other. Each of the plurality of detector components may be cooled by the cooling medium flowing in the corresponding pipe. Specifically, the cooling medium may simultaneously (almost simultaneously) absorb heat generated by each of the plurality of detector components, thereby evenly cooling the plurality of detector components, and avoiding (or reducing, or eliminating) a temperature gradient in different positions of the detector assembly.

It should be noted the above descriptions of the director module 112 may be provided for illustration purposes and not limit the scope of the present disclosure. In some embodiments, the detector module may include the detector assembly, the cover assembly, the at least one cooling assembly, the plurality of pipes, and the medium separation component as illustrated above.

The network 120 may include any suitable network that can facilitate the exchange of information and/or data for the imaging system 100. In some embodiments, one or more components of the imaging system 100 (e.g., the scanner 110, the terminal 130, the processing device 140, or the storage device 150) may communicate information and/or data with one or more other components of the imaging system 100 via the network 120. For example, the processing device 140 may generate a reconstructed image based on signal(s) acquired by the scanner 110 (e.g., the detector module 112) via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the terminal 130 may remotely operate the scanner 110 and/or the processing device 140. In some embodiments, the terminal 130 may operate the scanner 110 and/or the processing device 140 via a wireless connection. In some embodiments, the terminal 130 may receive information and/or instructions inputted by a user, and send the received information and/or instructions to the scanner 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

The processing device 140 may process data and/or information obtained from the scanner 110, the terminal 130, and/or the storage device 150. For example, the processing device 140 may generate a reconstructed image based on signal(s) acquired by the scanner 110 (e.g., the detector module 112). As another example, the processing device 140 may transmit an instruction for cooling the detector module 112 to a cooling assembly of the detector module 112. In some embodiments, the processing device 140 may be a single server or a server group. The server group may be centralized, or distributed. In some embodiments, the processing device 140 may be local or remote. For example, the processing device 140 may access information and/or data stored in or acquired by the scanner 110, the terminal 130, and/or the storage device 150 via the network 120. As another example, the processing device 140 may be directly connected to the scanner 110 (as illustrated by the bidirectional arrow in dashed lines connecting the processing device 140 and the scanner 110 in FIG. 1), the terminal 130 (as illustrated by the bidirectional arrow in dashed lines connecting the processing device 140 and the terminal 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

The storage device 150 may store data and/or instructions. In some embodiments, the storage device 150 may store data obtained from the scanner 110, the terminal 130 and/or the processing device 140. For example, the processing device 140 may generate a reconstructed image based on signal(s) acquired by the scanner 110 (e.g., the detector module 112), and then the reconstructed image may be stored in the storage device 150 for further use or processing. In some embodiments, the storage device 150 may store data obtained from the terminal 130 and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage devices may include a magnetic disk, an optical disk, a solid-state drive, etc. Exemplary removable storage devices may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the imaging system 100 (e.g., the scanner 110, the processing device 140, the terminal 130, etc.). One or more components of the imaging system 100 may access the data or instructions stored in the storage device 150 via the network 120. In some embodiments, the storage device 150 may be directly connected to or communicate with one or more components of the imaging system 100 (e.g., the scanner 110, the processing device 140, the terminal 130, etc.). In some embodiments, the storage device 150 may be part of the processing device 140.

In some embodiments, the imaging system 100 may further include one or more power supplies (not shown in FIG. 1) connected to one or more components of the imaging system 100 (e.g., the scanner 110, the processing device 140, the terminal 130, the storage device 150, etc.).

Figure 2:
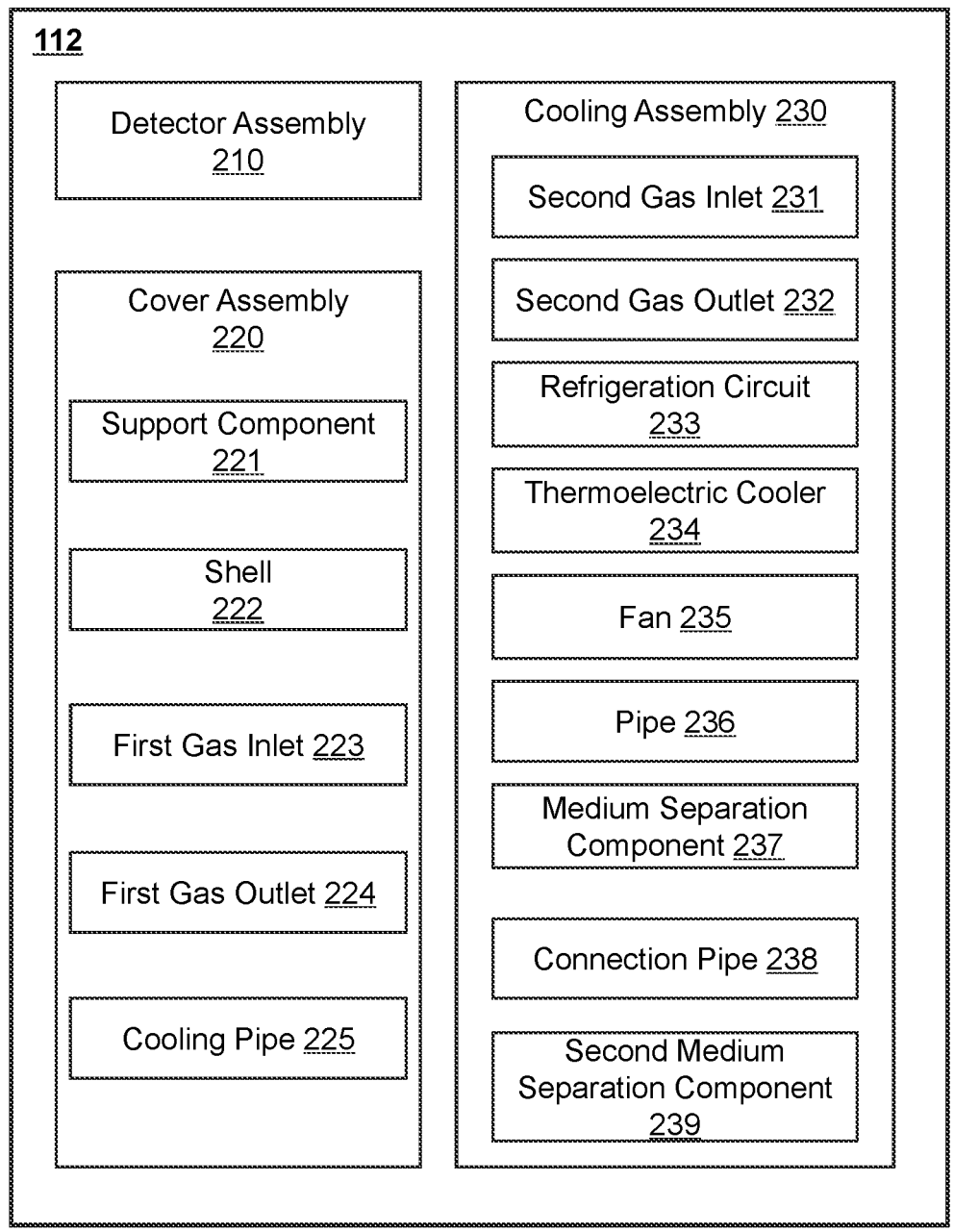
FIG. 2 is a block diagram illustrating an exemplary detector module according to some embodiments of the present disclosure.

FIG. 2 is a block diagram illustrating an exemplary detector module according to some embodiments of the present disclosure. As illustrated, the detector module 112 may include a detector assembly 210, a cover assembly 220, and at least one cooling assembly 230.

In some embodiments, the detector assembly 210 may include a plurality of detector components and be configured to detect signal(s) associated with an object (e.g., a patient), e.g., attenuated radioactive rays (e.g., X rays), radiation events (e.g., gamma photons), etc. Taking a CT apparatus as an example, the detector assembly 210 may receive attenuated X-rays passing through the object and detect signal(s) thereof. The detector assembly 210 may also process and/or transmit the signal(s) to other components of the imaging system 100 for image reconstruction. More descriptions of the detector assembly 210 can be found elsewhere in the present disclosure (e.g., FIGS. 5A-6B, 9-12, and the descriptions thereof).

In some embodiments, the cover assembly 220 may be configured to accommodate the detector assembly 210. In some embodiments, the cover assembly 220 may include a support component 221 and a shell 222. The support component 221 and the shell 222 may form a chamber to accommodate or enclose the detector assembly 210. In some embodiments, the support component 221 may be configured to support the detector assembly 210. The shell 222 may be operably coupled to the support component 221. It should be noted the support component 221 and the shell 222 may be used interchangeably. In some alternative embodiments, the shell 222 may be configured to support the detector assembly 210. More descriptions of the cover assembly 220 can be found elsewhere in the present disclosure (e.g., FIGS. 5A-6B and 9-13, and the descriptions thereof).

In some embodiments, the cooling assembly 230 may be configured to cool the detector assembly 210 by providing a cooling medium (e.g., gas, liquid) to the cover assembly 220. Specifically, the cooling medium may flow into the cover assembly 220 to absorb heat generated by the detector assembly 210. The heat-laden cooling medium may flow back to the cooling assembly 230 to be cooled for reuse. This process may be repeated to cool the detector assembly 210.

In some embodiments, the cooling assembly 230 may include a second gas inlet 231, a second gas outlet 232. The cover assembly 220 may also include a first gas inlet 223 and a first gas outlet 224. The first gas inlet 223, the first gas outlet 224, the second gas inlet 231, and the second gas outlet 232 may be configured to form a fluid communication between the cover assembly 220 and the cooling assembly 230. In some embodiments, the cooling assembly 230 may also include a refrigeration circuit 233, and/or a thermoelectric cooler 234. The refrigeration circuit 233 and/or the thermoelectric cooler 234 may be configured to provide the cooling medium. In some embodiments, the cooling assembly 230 may also include at least one fan 235. The fan 235 may be configured to regulate or accelerate a flow rate of the gas flowing between the cover assembly 220 and the cooling assembly 230. More descriptions of the cooling assembly 230 can be found elsewhere in the present disclosure (e.g., FIGS. 5A-8, and the descriptions thereof).

In some embodiments, the cooling assembly 230 may include a plurality of pipes 236, and a medium separation component 237. The pipes 236 may be arranged in the plurality of detector components, respectively. The medium separation component 237 may be operably coupled to the pipes 236. The medium separation component 237 may be configured to distribute the cooling medium into the pipes 236. Each of the pipes 236 may be configured to guide a portion of the cooling medium to flow through a corresponding detector component of the plurality of detector components and cool the corresponding detector component. In some embodiments, the pipes 236 may be independent from each other and disconnected with each other. Each of the plurality of detector components may be cooled by the cooling medium flowing in a corresponding pipe. More descriptions of the cooling assembly 230 can be found elsewhere in the present disclosure (e.g., FIGS. 9-13, and the descriptions thereof).

In some embodiments, the cooling assembly 230 may include a second medium separation component 239 and a plurality of connection pipes 238. The second medium separation component 239 may be configured to distribute the cooling medium into a plurality of cooling pipes 225 arranged in the cover assembly 220 (e.g., the support component 221). The connection pipes 238 may be operably coupled to the second medium separation component 239 and the cooling pipes 225. The connection pipes 238 may be configured to allow the cooling medium to flow between the cooling pipes 225 and the second medium separation component 239. More descriptions of the cooling assembly 230 can be found elsewhere in the present disclosure (e.g., FIGS. 14-15, and the descriptions thereof).

It should be noted the above descriptions of the detector module 112 may be provided for illustration purposes and not limit the scope of the present disclosure. For persons having ordinary skills in the art, multiple variations and modifications may be made under the teachings of the present disclosure. However, those variations and modifications do not depart from the scope of the present disclosure. In some embodiments, the cooling assembly 230 of the detector module 112 may include the second gas inlet 231, the second gas outlet 232, the refrigeration circuit 233, and/or the fan 235. In some embodiments, the cooling assembly 230 of the detector module 112 may include the second gas inlet 231, the second gas outlet 232, the thermoelectric cooler 234, and/or the fan 235. In some embodiments, the cooling assembly 230 of the detector module 112 may include the pipes 236 and the medium separation component 237. In some embodiments, the cover assembly 220 of the detector module 112 may include the support component 221 and the shell 222. In some embodiments, the cover assembly 220 of the detector module 112 may include the support component 221, the shell 222, the first gas inlet 223, and the first gas outlet 224. In some embodiments, the cooling assembly 230 of the detector module 112 may include the second medium separation component 239 and the connection pipes 238. The cover assembly 220 of the detector module 112 may include the cooling pipes 225.

Figure 3:
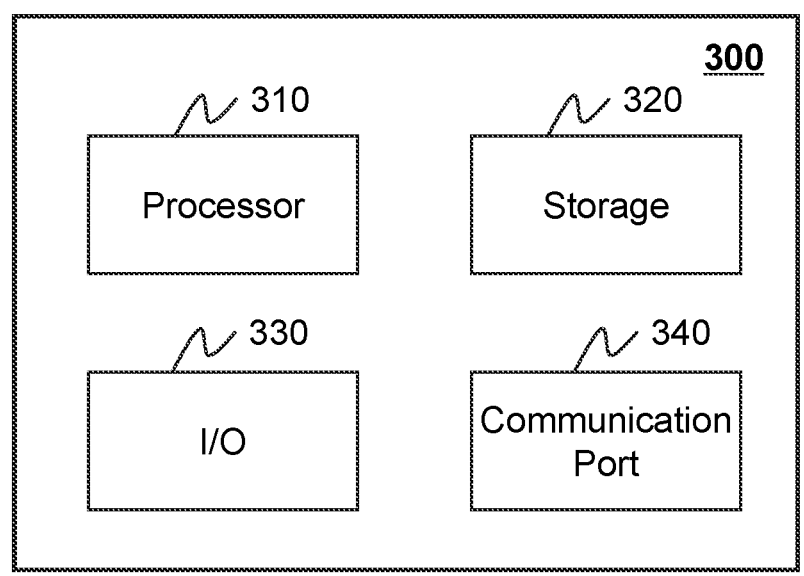
FIG. 3 is a schematic diagram illustrating exemplary hardware and/or software components of a computing device according to some embodiments of the present disclosure.

FIG. 3 is a schematic diagram illustrating exemplary hardware and/or software components of a computing device 300 on which the processing device 140 may be implemented according to some embodiments of the present disclosure. As illustrated in FIG. 3, the computing device 300 may include a processor 310, a storage 320, the input/output (I/O) 330, and a communication port 340.

The processor 310 may execute computer instructions (program code) and perform functions of the processing device 140 in accordance with techniques described herein. The computer instructions may include routines, programs, objects, components, signals, data structures, procedures, modules, and functions, which perform particular functions described herein. For example, the processor 310 may obtain, from the storage device 150 and/or the terminal 130, a reconstructed image based on signal(s) acquired by the scanner 110 (e.g., the detector module 112). In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 300. However, it should be noted that the computing device 300 in the present disclosure may also include multiple processors, and thus operations of a method that are performed by one processor as described in the present disclosure may also be jointly or separately performed by the multiple processors. For example, if in the present disclosure the processor of the computing device 300 executes both operations A and B, it should be understood that operations A and step B may also be performed by two different processors jointly or separately in the computing device 300 (e.g., a first processor executes operation A and a second processor executes operation B, or the first and second processors jointly execute operations A and B).

The storage 320 may store data/information obtained from the scanner 110, the terminal 130, the storage device 150, or any other component of the imaging system 100. In some embodiments, the storage 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program for reconstructing an image based on signal(s) acquired by the scanner 110 (e.g., the detector module 112).

The I/O 330 may input or output signals, data, or information. In some embodiments, the I/O 330 may enable user interaction with the processing device 140. In some embodiments, the I/O 330 may include the input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected to a network (e.g., the network 120) to facilitate data communications. The communication port 340 may establish connections between the processing device 140 and the scanner 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
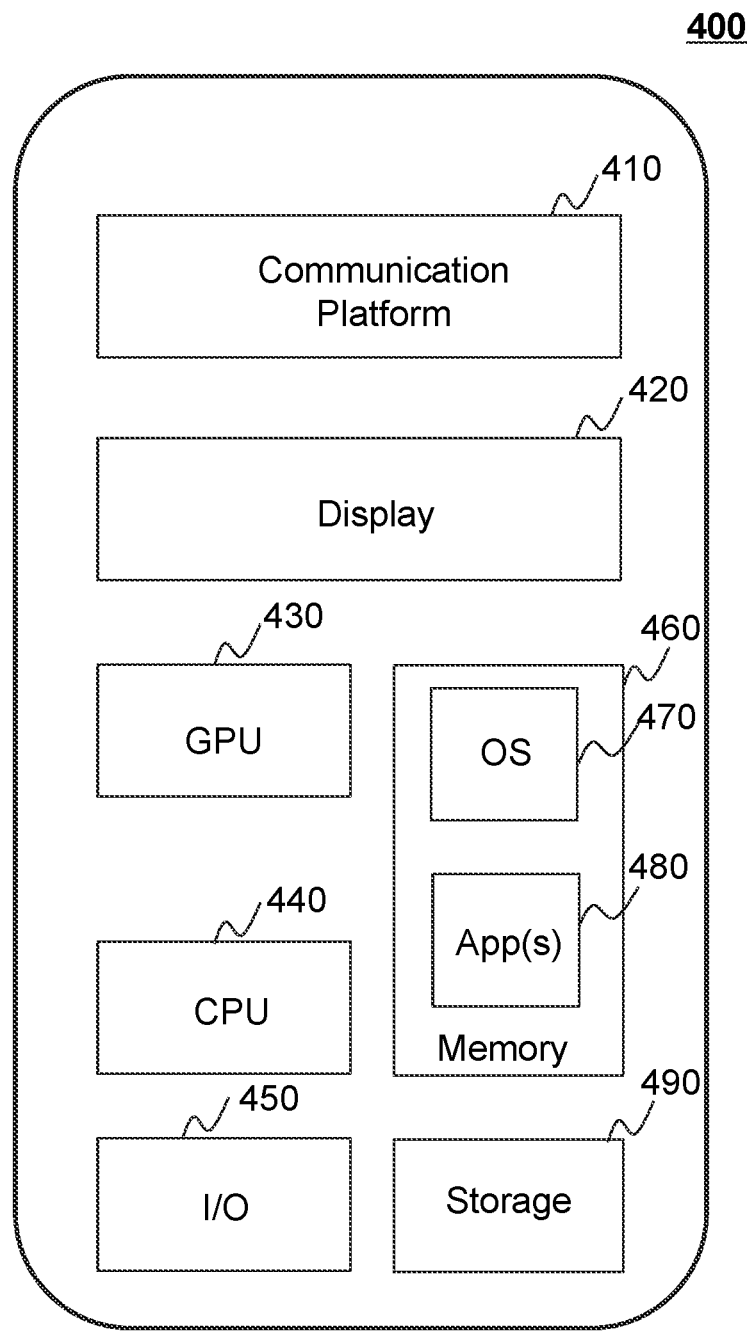
FIG. 4 is a schematic diagram illustrating exemplary hardware and/or software components of a mobile device 400 according to some embodiments of the present disclosure.

FIG. 4 is a schematic diagram illustrating exemplary hardware and/or software components of a mobile device on which the terminal 130 may be implemented according to some embodiments of the present disclosure. As illustrated in FIG. 4, the mobile device 400 may include a communication platform 410, a display 420, a graphic processing unit (GPU) 430, a central processing unit (CPU) 440, an I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 5A:
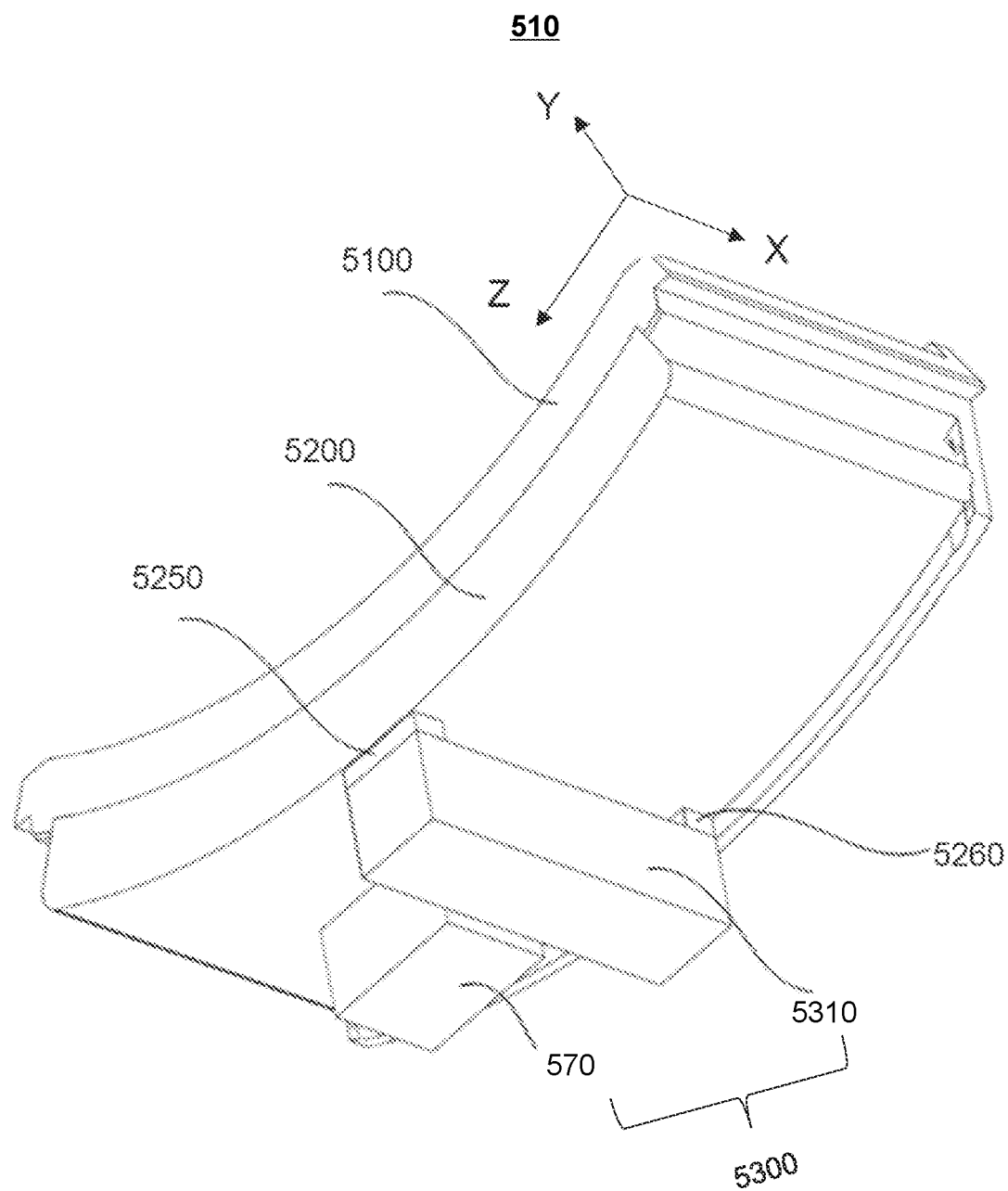
FIG. 5A illustrates an exterior structure of a part of an exemplary detector module according to some embodiments of the present disclosure.
Figure 5B:
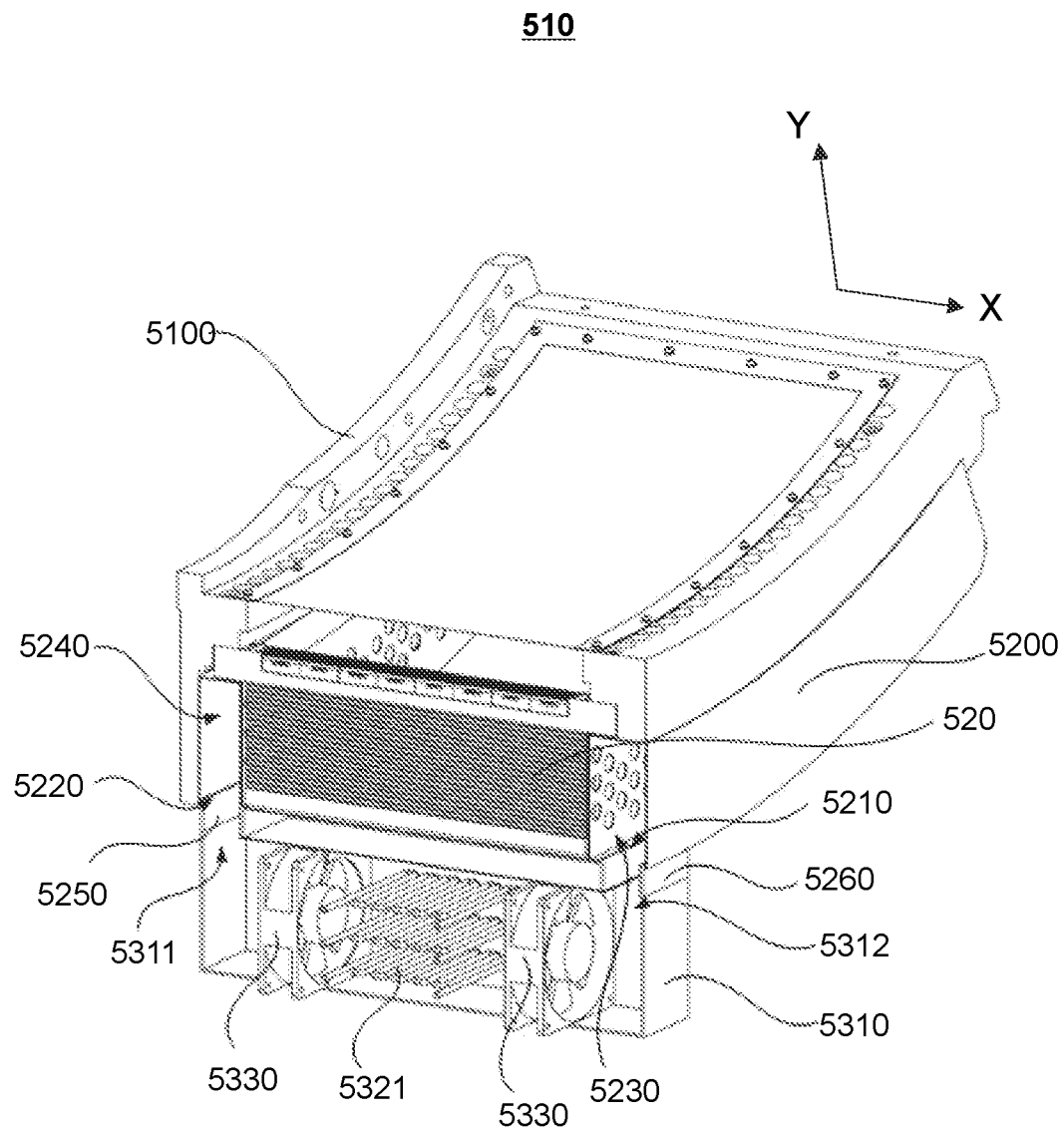
FIG. 5B illustrates an interior structure of a part of an exemplary detector module according to some embodiments of the present disclosure.

FIG. 5A illustrates an exterior structure of a part of an exemplary detector module according to some embodiments of the present disclosure. FIG. 5B illustrates an interior structure of a part of an exemplary detector module according to some embodiments of the present disclosure.

As illustrated in FIG. 5A, the detector module 510 may include a support component 5100, a shell 5200, and at least one cooling assembly 5300. The detector module 510 may also include a detector assembly (not shown). In some embodiments, the detector assembly may include a plurality of detector components. A detector component 520 as illustrated in FIG. 5B may be an exemplary detector component. The detector assembly (i.e., the plurality of detector components) may be configured to detect signal(s) associated with an object (e.g., a patient), e.g., attenuated radioactive rays (e.g., X rays), radiation events (e.g., gamma photons), etc. Taking a CT apparatus as an example, the detector assembly may receive attenuated X-rays passing through the object and detect signal(s) thereof. The detector assembly may also process and/or transmit the signal(s) to other components of the imaging system 100 for image reconstruction.

As used herein, the support component 5100 and the shell 5200 may be collectively referred to as a "cover assembly". The cover assembly may be configured to accommodate the detector assembly. The support component 5100 may be configured to support the detector assembly. In some embodiments, the support component 5100 and the shell 5200 may form a chamber to enclose the detector assembly. In some embodiments, the shapes of a cross section of the support component 5100 and a cross section of the shell 5200 may be mutually fitted to form the chamber. For example, cross sections (e.g., in the XY plane) of the support component 5100 and the shell 5200 may have an arcuate shape, a square shape, a trapezoid shape, etc. In some embodiments, The X-axis direction may refer to a direction along which an object is moved into and/or out of the scanner 110. The Y-axis direction may refer to a radial direction of a rotary frame of the tube 111. The Z-axis direction may refer to a direction perpendicular to the Y-axis direction and the Y-axis direction.

It should be noted that a detector component may include a packaged detector as the minimum mounting unit, thereby easily mounting, detaching, and/or maintaining the detector component. The detector assembly may include all packaged detectors (i.e., the plurality of detector components) inside the cover assembly. The detector assembly (i.e., the plurality of detector components, the packaged detectors) may be arranged along a length direction of the cover assembly (e.g., the Z-axis direction as illustrated in FIG. 5A).

In some embodiments, the support component 5100 may provide a main support structure for the detector module 510 and/or be used as a base for mounting the detector assembly. The shell 5200 may be operably coupled to the support component 5100. For example, the detector assembly may be mounted on the support component 5100 by welding, embedding, through one or more mechanical fasteners (e.g., a bolt, a screw, a nut, a gasket, an airtight glue, an airtight adhesive tape), or the like, or a combination thereof. It should be noted the support component 5100 and the shell 5200 may be used interchangeably. In some alternative embodiments, the shell 5200 may provide a main support structure for the detector module 510 and/or be used as a base for mounting the detector assembly.

Figure 9:
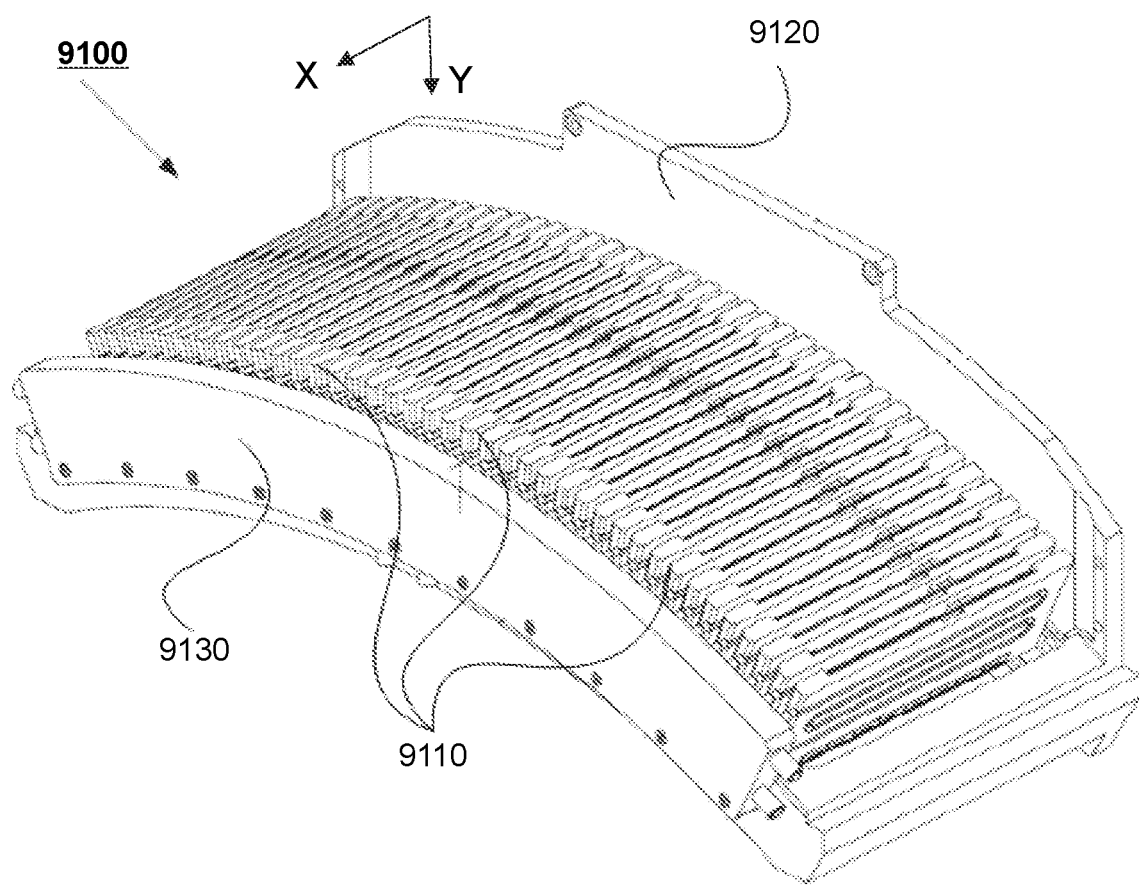
FIGS. 9-10 illustrate different views of an exemplary detector module according to some embodiments of the present disclosure.

In some embodiments, the plurality of detector components may be arranged inside the cover assembly (e.g., the chamber formed by the support component 5100 and the shell 5200) along the length direction (e.g., a circumferential direction, or a rotation direction) of the cover assembly (e.g., along the Z-axis direction as illustrated in FIG. 5A). The orientation of each of the plurality of detector components may be parallel (or substantially parallel) to a width direction (e.g., the X-axis direction as illustrated in FIG. 5A) of the cover assembly. As shown in FIG. 9, the orientation of each of the detector components 9110 may be parallel (or substantially parallel) to a width direction (e.g., the X-axis direction as illustrated in FIG. 9) of the cover assembly (e.g., the support component 9120). Specifically, a length direction of each of the plurality of detector components (e.g., the detector component 520 in FIG. 5B) may extend along the width direction of the cover assembly. A width direction of each of the plurality of detector components may extend along the length direction of the cover assembly. In some embodiments, a length direction and a width direction of the detector assembly may be different from the length direction and the width direction of each detector component, respectively. For illustration purposes, the length direction of the detector assembly may extend along the length direction of the cover assembly. The width direction of the detector assembly may extent along the width direction of the cover assembly.

In some embodiments, when the detector assembly implements functions e.g., receiving the attenuated rays, detecting, processing and/or transmitting the signal(s), the detector assembly may generate a great amount of heat. If the heat is accumulated to a certain extent, the detector module 510 may fail to function properly and the signal(s) may become inaccurate, thereby affecting the accuracy of the image(s) reconstructed based on the inaccurate signal(s). In some embodiments, the cooling assembly 5300 may cool the detector module 510 so that the temperatures of different portions of the detector module 510 may be maintained at an acceptable temperature level and the detector assembly may function properly. The cooling assembly 5300 may be configured to cool the detector assembly by providing a cooling medium (e.g., a gas, a fluid) to the cover assembly. In some embodiments, the cooling assembly 5300 may be configured to cool the cooling medium circulating between the shell 5200 and a cover 5310 of the cooling assembly 5300.

In some embodiments, the detector module 510 may further include a first connection passage 5250 and/or a second connection passage 5260. As illustrated in FIGS. 5A-5B, the first connection passage 5250 and the second connection passage 5260 may be located between the cover assembly and the cooling assembly 5300. The first connection passage 5250 and the second connection passage 5260 may have a hollow structure so that the cooling medium may flow between the cooling assembly 5300 and the cover assembly through the first connection passage 5250 and the second connection passage 5260.

In some embodiments, the cooling assembly 5300 may be operably coupled to cover assembly (e.g., the shell 5200). For illustration purposes, the cooling assembly 5300 may be operably coupled to the cover assembly (e.g., the shell 5200) at least through the first connection passage 5250 and the second connection passage 5260. For illustration purposes, a cooling component 570 (e.g., the refrigeration circuit 7320 in FIGS. 7-8) of the cooling assembly 5300 may be operably coupled to the cover assembly, e.g., by welding, embedding, through one or more mechanical fasteners (e.g., a bolt, a screw, a nut, a gasket, an airtight glue, an airtight adhesive tape), etc. It should be noted that the cooling assembly 5300 may be located at any portion of the detector module 510. A second gas inlet 5311 and a second gas outlet 5312 of each of the at least one cooling assembly 5300 may be operably coupled to the cover assembly. For example, a cover 5310 of the cooling assembly 5300 and/or the cooling component 570 may be operably coupled to the support component 5100.

In some embodiments, the cover 5310 of the cooling assembly 5300 may be operably coupled to the shell 5200 through the first connection passage 5250 and the second connection passage 5260. The first connection passage 5250 and the second connection passage 5260 may facilitate and/or strengthen the connection between the cooling assembly 5300 and the cover assembly. In some embodiments, the cover assembly and the cooling assembly 5300 may have or form a sealed structure. The first connection passage 5250 and the second connection passage 5260 may be airtightly coupled to the cover assembly and the cooling assembly 5300. Thus, the gas inside the cover assembly and the cooling assembly 5300 may not exchange with the gas outside the detector module 510. The gas inside the cover assembly and/or the cooling assembly 5300 may quickly decrease to an acceptable temperature level to cool the detector assembly.

In some embodiments, the cooling medium may randomly flow through the shell 5200 (e.g., the detector assembly). In some embodiments, the detector module 510 may be designed to allow the cooling medium to flow inside the shell 5200 along a predetermined path. For example, the cooling medium may flow through the shell 5200 along a length direction (e.g., a circumferential direction, or a rotation direction) of the cover assembly (e.g., the Z-axis direction as illustrated in FIG. 5A). As another example, the cooling medium may flow through the shell 5200 along a width direction of the cover assembly (e.g., the X-axis direction as illustrated in FIG. 5A). As a further example, the cooling medium may simultaneously flow through the shell 5200 along the width direction of the cover assembly and the length direction (e.g., a circumferential direction, or a rotation direction) of the cover assembly.

As illustrated in FIG. 5B, the detector module 510 may be designed to allow the cooling medium to flow through the shell 5200 along the width direction of the cover assembly. The cover assembly (e.g., the shell 5200) may include a first gas inlet 5210 and a first gas outlet 5220 configured to guide the cooling medium (e.g., gas) to pass through the shell 5200. The first gas inlet 5210 and the first gas outlet 5220 may be arranged along the width direction of the cover assembly. Accordingly, the cooling medium may pass the detector assembly along the width direction of the cover assembly. The distance of the cooling medium flowing and/or circulating inside the shell 5200 may be relatively short along the width direction and quickly reach and cool the plurality of detector components, and avoiding (or reducing, or eliminating) the temperature gradient in different positions of the detector assembly.

The cooling assembly 5300 may include the cover 5310. The cover 5310 may include a second gas inlet 5311 and a second gas outlet 5312. The first gas inlet 5210, the first gas outlet 5220, the second gas inlet 5311, and the second gas outlet 5312 may be configured to form a fluid communication between the cover assembly and the cooling assembly 5300 to guide the cooling medium to cool the detector assembly.

In some embodiments, the second gas inlet 5311 may be operably coupled to the first gas outlet 5220. The second gas outlet 5312 may be operably coupled to the first gas inlet 5210. In some embodiments, the second gas inlet 5311 may be operably coupled to the first gas outlet 5220 through the second connection passage 5260. The second connection passage 5260 may guide the heat-laden cooling medium to flow from the first gas outlet 5220 to the second gas inlet 5311, and then back to the cooling assembly 5300. In some embodiments, the second gas outlet 5312 may be operably coupled to the first gas inlet 5210 through the first connection passage 5250. The first connection passage 5250 may guide the cooling medium to flow from the second gas outlet 5312 to the first gas inlet 5210, and then into the cover assembly to cool the detector assembly.

For illustration purposes, the second gas inlet 5311 may be operably coupled to the first gas outlet 5220 through the second connection passage 5260. Specifically, a first end of the second connection passage 5260 may be operably coupled to the second gas inlet 5311. A second end of the second connection passage 5260 may be operably coupled to the first gas outlet 5220. For illustration purposes, the second gas outlet 5312 may be operably coupled to the first gas inlet 5210 through the first connection passage 5250. Specifically, a first end of the first connection passage 5250 may be operably coupled to the second gas outlet 5312. A second end of the second connection passage 5260 may be operably coupled to the first gas inlet 5210.

In some embodiments, as illustrated in FIG. 5B, the detector module 510 may also include a gas inlet chamber 5230 located inside the cover assembly (e.g., the shell 5200. The first gas inlet 5210 may be in fluid communication with the gas inlet chamber 5230. Specifically, the cooling medium may flow into the gas inlet chamber 5230 via the first gas inlet 5210. That is, the first gas inlet 5210 may introduce the cooling medium into the gas inlet chamber 5230.

Figure 6A:
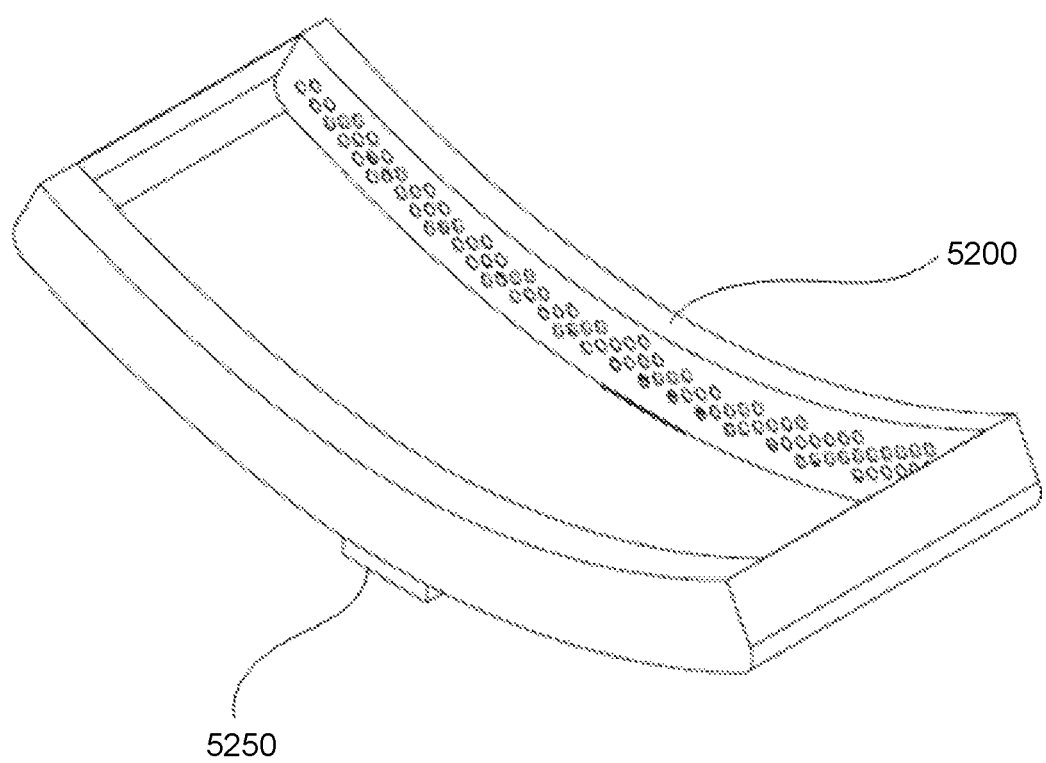
FIGS. 6A-6B illustrate an exemplary shell according to some embodiments of the present disclosure.
Figure 6B:
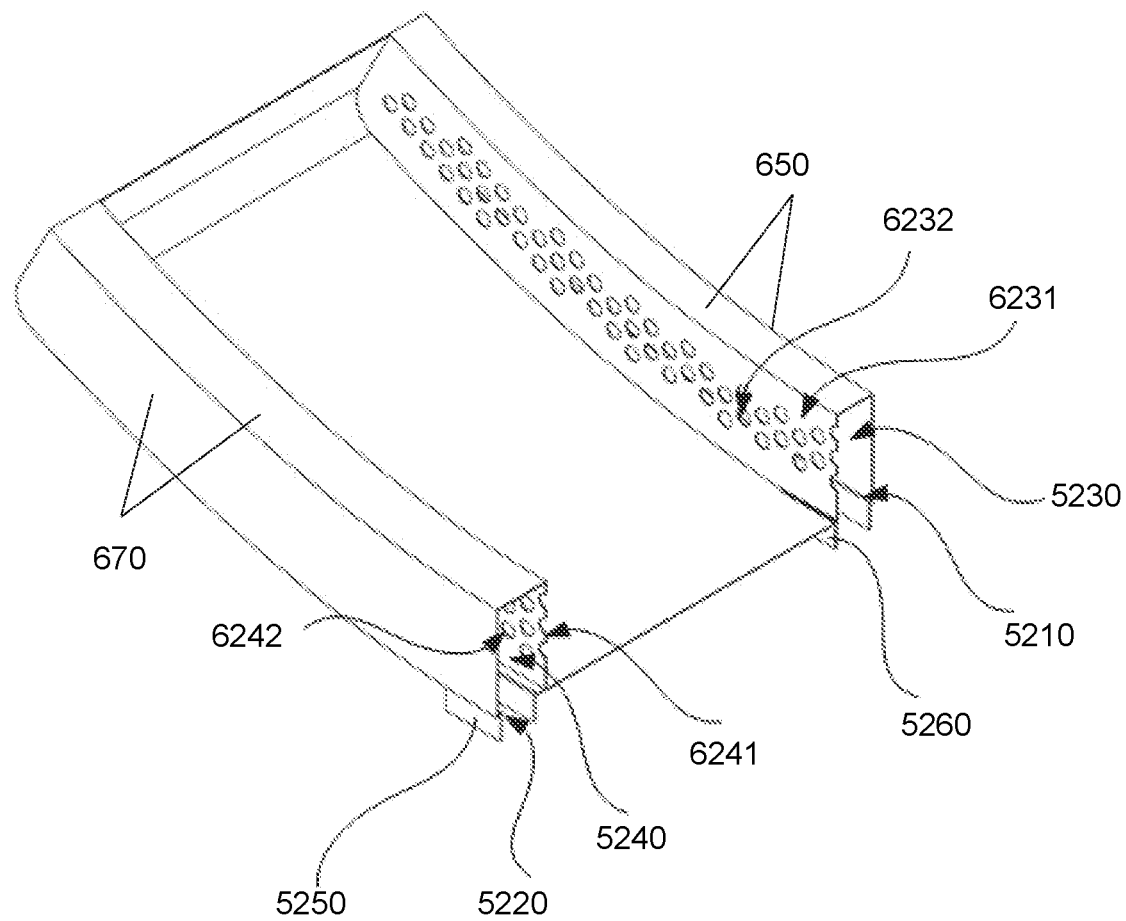

FIGS. 6A-6B illustrate the shell 5200 according to some embodiments of the present disclosure. As illustrated, the gas inlet chamber 5230 may be arranged along the length direction (e.g., a circumferential direction, or a rotation direction) of the cover assembly. The gas inlet chamber 5230 may be disposed in the cover assembly (e.g., the shell 5200). Specifically, the gas inlet chamber 5230 may include two sidewalls 650. The two sidewalls 650 of the gas inlet chamber 5230 may function as two sidewalls of the shell 5200. The gas inlet chamber 5230 may also include a sidewall 6231. The sidewall 6231 may be configured to allow (or guide) the cooling medium to flow into the detector assembly. The sidewall 6231 of the gas inlet chamber 5230 may include one or more holes 6232. The cooling medium may pass the sidewall 6231 through the hole(s) 6232 and reach the detector assembly. In some embodiments, the hole(s) 6232 may be evenly spaced at the sidewall 6231. Accordingly, the cooling medium inside the gas inlet chamber 5230 may reach the plurality of detector components through the hole(s) 6232 arranged along the length direction of the cover assembly.

As illustrated above, the plurality of detector components may be arranged along the length direction of the cover assembly. Because the gas inlet chamber 5230 can be arranged along the length direction of the cover assembly, the gas inlet chamber 5230 may guide the cooling medium quickly reach each space of the gas inlet chamber 5230. Accordingly, the cooling medium may flow through the hole(s) 6232, along the width direction of the cover assembly, and quickly reach each of the plurality of detector components after passing through corresponding hole(s) 6232 Specifically, the cooling medium may simultaneously (almost simultaneously) absorb heat generated by each of the plurality of detector components, thereby evenly cooling the plurality of detector components, and avoiding (or reducing, or eliminating) the temperature gradient in different positions of the detector assembly.

In some embodiments, the detector module 510 may also include a gas outlet chamber 5240 located inside the cover assembly (e.g., the shell 5200). The first gas outlet 5220 may be in fluid communication with the gas outlet chamber 5240. Specifically, the cooling medium may flow from the first gas outlet 5220 into the gas outlet chamber 5240. In some embodiments, the cooling medium flowing from the gas inlet chamber 5230 may pass through the detector assembly (e.g., along the width direction of the cover assembly) and absorb heat from the detector assembly. Then the heat-laden cooling medium may flow out of the detector assembly into the gas outlet chamber 5240. In some embodiments, the heat-laden cooling medium may further flow back to the cooling assembly 5300 to be cooled for reuse. This process may be repeated to cool the detector assembly.

As illustrated in FIGS. 6A-6B, the gas outlet chamber 5240 may be arranged along the length direction (e.g., a circumferential direction, or a rotation direction) of the cover assembly. The gas outlet chamber 5240 may be disposed in the cover assembly (e.g., the shell 5200). Specifically, the gas outlet chamber 5240 may include two sidewalls 670. The two sidewalls 670 of the gas outlet chamber 5240 may function as two sidewalls of the shell 5200. The gas outlet chamber 5240 may also include a sidewall 6241. The sidewall 6241 may be configured to allow (or guide) the cooling medium to flow out of the detector assembly. The sidewall 6241 of the gas outlet chamber 5240 may include one or more holes 6242. The cooling medium may flow out of the detector assembly and pass the sidewall 6241 through the hole(s) 6242. In some embodiments, the hole(s) 6242 may be evenly spaced at the sidewall 6241. The heat-laden cooling medium may flow away from the detector assembly and into the gas outlet chamber 5240 arranged along the length direction of the cover assembly through the hole(s) 6242.

The cooling assembly 5300 may provide (or generate) the cooling medium. The cooling medium may flow from the cooling assembly 5300 into the gas inlet chamber 5230 via the second gas outlet 5312, the first connection passage 5250, and the first gas inlet 5210. The cooling medium may flow into the gas inlet chamber 5230 through the first gas inlet 5210. Then the cooling medium may reach the detector assembly through the hole(s) 6232 and absorb heat generated by the detector assembly. Further, the heat-laden cooling medium may flow away from the detector assembly into the gas outlet chamber 5240 through the hole(s) 6242. The heat-laden cooling medium may flow back to the cooling assembly 5300 to be cooled for reuse. Specifically, the heat-laden cooling medium collected in the gas outlet chamber 5240 may flow sequentially through the first gas outlet 5220, the second connection passage 5260, and the second gas inlet 5311, and then reach the cooling assembly 5300. This process may be repeated to cool the detector assembly, thereby cooling the detector assembly quickly and evenly. As illustrated above, the plurality of detector components may be arranged along the length direction of the cover assembly. Besides, the gas inlet chamber 5230 and the gas outlet chamber 5240 may be located at two sides of the detector assembly along the length direction. The cooling medium may reach each of the plurality of detector components from the hole(s) 6232 at the same (or substantially the same) time. The heat-laden cooling medium may flow away from the plurality of detector components from the hole(s) 6242. Therefore, the cooling medium may efficiently and quickly cool the entire detector assembly, thereby avoiding overheating of the detector assembly, and/or the temperature gradient in different positions of the detector assembly.

In some cases, one or more detector components at a central region of the detector assembly may generate more heat than one or more detector components close to the end(s) of the detector assembly. In some embodiments, the central region and the end(s) of the detector assembly may be defined along the length direction and/or the width direction of the detector assembly. For example, the central region may be defined as a region in the middle along the length direction of the detector assembly and having a length being a certain portion (e.g., ½, ⅓, ¼) of the length of the detector assembly. In some embodiments, the number (or count) of the detector component(s) at the central region may be a specific value, e.g., a value from 5 to 15, etc. The remaining detector components may belong to one or more other regions (e.g., the detector component(s) close to the end(s) of the detector assembly may belong to "end regions"). Each region may include a second specific number (or count, e.g., a value from 5 to 15) of detector components. In some alternative embodiments, the detector assembly may be evenly divided into a plurality of regions. The number (or count) of the detector component(s) in each region may be the same. At least one of the plurality of regions in the middle of the detector assembly may be referred to as the central region. The remaining regions of the plurality of regions may be referred to as "end regions", respectively. For example, the detector assembly may be evenly and sequentially divided into 3 regions, i.e., a first region, a second region, and a third region. The second region may be referred to as the central region.

Figure 11:
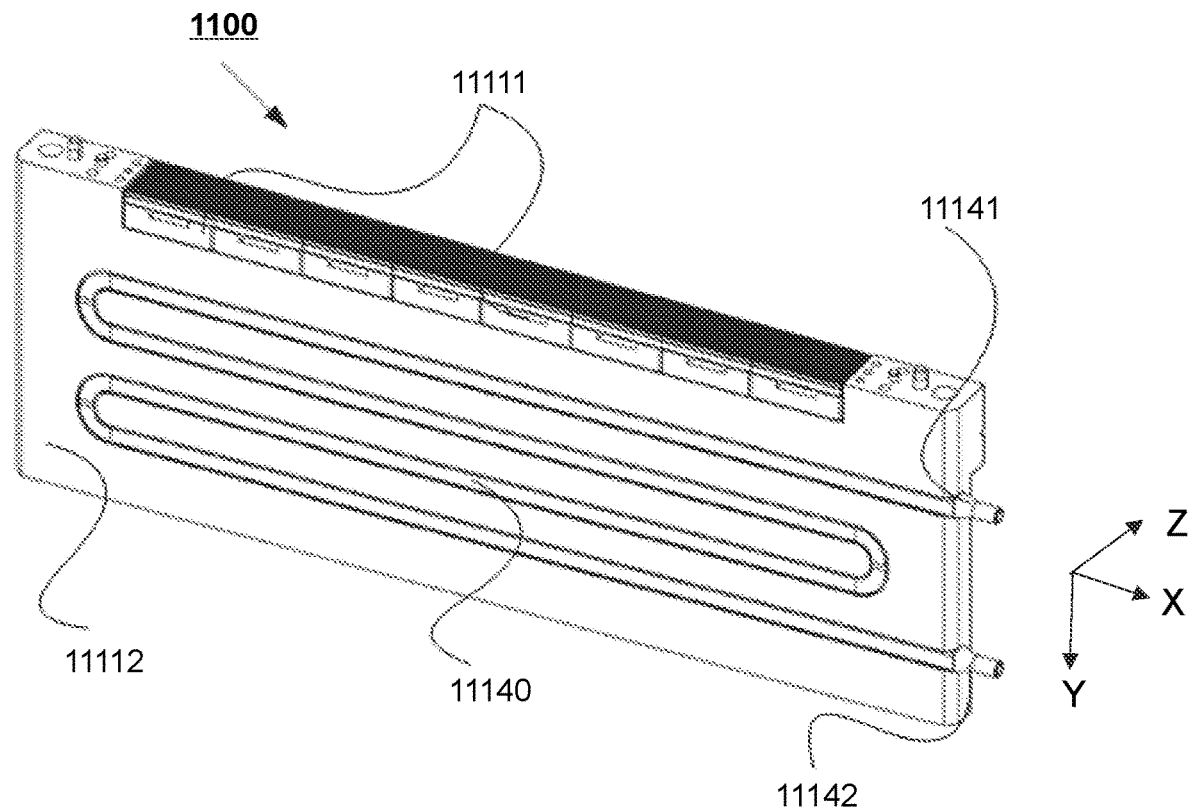
FIG. 11 illustrates an exemplary detector component according to some embodiments of the present disclosure.

In order to further evenly cooling the plurality of detector components, the amount (or flow rate) of the cooling medium passing through the detector component(s) at the central region may be regulated to be greater than the amount (or flow rate) of the cooling medium passing through the detector component(s) close to the end(s) of the detector assembly. In some embodiments, a first average count of holes through which the cooling medium passes to reach the detector component(s) close to the end(s) of the detector assembly may be smaller than or equal to a second average count of holes through which the cooling medium passes to reach the detector component(s) at the central region of the detector assembly. In some embodiments, an average opening size of the holes through which the cooling medium passes to reach the detector component(s) close to the end(s) of the detector assembly may be smaller than or equal to a second average opening size of the holes through which the cooling medium passes to reach the detector component(s) at the central region of the detector assembly. It should be noted that the hole(s) 6242 and/or the hole(s) 6232 may be replaced by one or more conduits. In some embodiments, the conduit(s) may be inside the plurality of detector components to guide the cooling medium to pass through to cool the plurality of detector components. For example, the conduit(s) may include a plurality of pipes 11140 as illustrated in FIG. 11. In some embodiments, the detector components may be spaced with each other inside the chamber. For example, two adjacent detector components may include a gap therebetween. The conduit(s) may be disposed between the detector components e.g., in the gaps. In some embodiments, the cooling medium may be a cooling liquid (e.g., water, oil).

Figure 7:
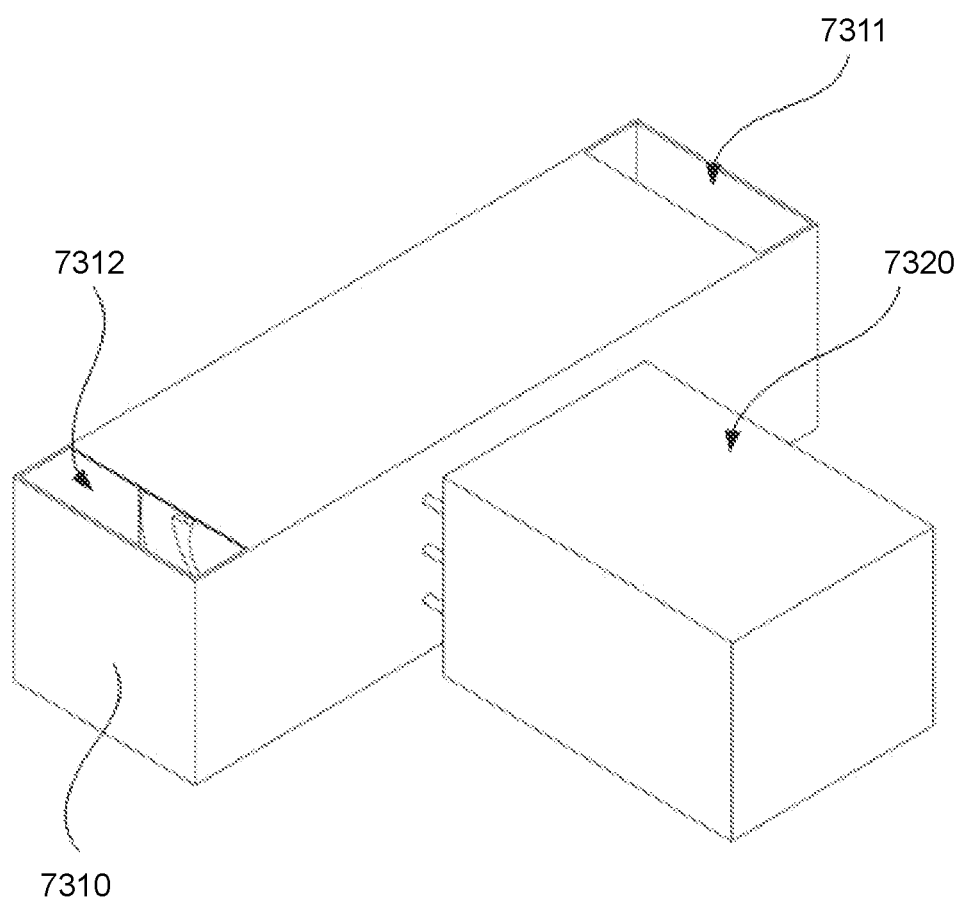
FIG. 7-8 illustrate an exemplary cooling assembly according to some embodiments of the present disclosure.

As shown in FIGS. 5A-5B, the cooling assembly 5300 may include the cooling component 570 and the cover 5310. The cooling component 570 may be configured to generate the cooling medium and/or cool down the heat-laden cooling medium. For example, the cooling component 570 may include a refrigeration circuit (e.g., the refrigeration circuit 7320 as illustrated in FIG. 7), a thermoelectric cooler (TEC), etc. The refrigeration circuit may include an evaporator 5321 configured to provide the cooling medium. In some embodiments, the evaporator 5321 may be located inside the cover 5310. In some embodiments, the refrigeration circuit may also include a condenser and/or a compressor. In some embodiments, the compressor may use a cryogen and/or a refrigerant to cool the cooling medium. The compressor (also referred to as a heat exchanger) may increase the pressure of the cryogen, and then, the cryogen may be condensed, and the heat in the cryogen may dissipate to a heat sink. In some embodiments, condensed cryogen may evaporate in the evaporator 5321, and absorb heat from the cooling medium, and then the cooling medium may be cooled down. In some embodiments, the compressor may include a shell and a heat exchanger (e.g., a tube heat exchanger, a pillow plate heat exchanger, a fluid heat exchanger, a dynamic scraped surface heat exchanger, a phase-change heat exchanger, a direct contact heat exchanger, or the like, or any combination thereof). When the refrigeration circuit (e.g., the evaporator 5321) provides the cooling medium, the condenser and/or the compressor may generate heat which may decrease the cooling efficiency in cooling the detector assembly. In order to reduce undesired heat absorption of the cooling medium, the condenser and/or the compressor may be located outside the cover 5310.

In some embodiments, the structure of the TEC may be simple. The TEC may include a cold side located inside the cover 5310. The cold side may be configured to cool the cooling medium (e.g., a gas) flowing between the cover assembly and the cooling assembly 5300 (e.g., the cover 5310). The TEC may also include a hot side located outside the cover 5310 to reduce undesired heat absorption of the cooling medium. More descriptions of the cooling assembly 5300 can be found elsewhere in the present disclosure (e.g., FIGS. 7-8 and the descriptions thereof).

The cooling assembly 5300 may also include at least one fan configured to regulate or accelerate a flow rate of the gas flowing between the cover assembly and the cooling assembly 5300. In some embodiments, the flow rate may be regulated or accelerated by regulating the rotation speed of the at least one fan, the number (or count) of the at least one fan, the position of the at least one fan. In some embodiments, one of the at least one fan may be located inside the cover 5310. In some embodiments, one of the at least one fan may be set near to the cooling component 570. In some embodiments, one of the at least one fan may be set near to the first gas inlet 5210, the second gas outlet 5312, the first gas outlet 5220, and/or the second gas inlet 5311. As illustrated above, the cooling component 570 may provide or generate the cooling medium. By arranging the at least one fan near to the cooling component 570, the first gas inlet 5210, the second gas outlet 5312, the first gas outlet 5220, and/or the second gas inlet 5311, the at least one fan may more efficiently regulate or accelerate the flow rate of the gas flowing between the cover assembly and the at least one cooling assembly 5300. It should be noted that the number (or count) of the at least one fan may be non-limiting, e.g., 1, 2, or more. By increasing the number (or count) of the at least one fan, the flow rate of the cooling medium may increase and the efficiency in cooling the detector assembly may increase. As illustrated in FIG. 5B, the cooling assembly 5300 may include two fans 5330, i.e., a first fan, a second fan. The cooling component 570 may be located between the fans 5330. The first fan may be located near the second gas outlet 5312. The cooling medium may be blew into the cover assembly by the first fan via the second gas outlet 5312. The second fan may be located near the second gas inlet 5311. The heat-laden cooling medium may be blew into the cooling assembly 5300 by the second fan via the second gas inlet 5311.

In some embodiments, the cover assembly and the cooling assembly 5300 may have or form sealed structure(s), thereby protecting components (e.g., the detector assembly) inside the cover assembly and the cooling assembly 5300 from dust and dirt or being collided by a component external to the cover assembly and the cooling assembly 5300. Therefore, the service life, the stability, and/or work efficiency of the detector module 510 may be improved. In some embodiments, for a CT apparatus, the detector module 510 may be attached to or fixed on a frame assembly (e.g., a rotary frame) of the CT apparatus through the cover assembly (e.g., the support component 5100). In some embodiments, the cover assembly may be made of a heat-conductive material (e.g., a metallic material, or the like), thereby conducting at least a portion of the heat generated by the detector assembly to other components of the detector module 510, and further facilitating the cooling of the detector assembly.

It should be noted the number (or count) of the cooling assembly 5300 of the detector module 510 may be non-limiting, and be set according to practical needs, e.g., the amount of heat generated by the detector assembly, the duration and/or frequency of using the detector assembly, the time for cooling the detector assembly, etc. In some embodiments, the detector module 510 may include one cooling assembly, e.g., the cooling assembly 5300 as illustrated in FIGS. 5A-5B. In some embodiments, the cooling assembly 5300 may be located at a central region of the shell 5200. In some alternative embodiments, the detector module 510 may include a plurality of cooling assemblies. For illustration purposes, when the size of the detector module 510 and/or detector assembly is relatively large, the detector module 510 may include 2, 3, or more cooling assemblies. At least one of the 2, 3, or more cooling assemblies may be located at a central region of the shell 5200. The structure of each of the plurality of cooling assemblies may be the same as or similar to the cooling assembly 5300. Each of the plurality of cooling assemblies may include a cooling component (e.g., the cooling component 570) and/or at least one fan (e.g., the fan 5330). In some embodiments, each of the plurality of cooling assemblies may include a cover similar to the cover 5310. The cover of each cooling assembly may be connected to the shell 5200. In some embodiments, the plurality of cooling assemblies may share the cover 5310. The cover 5310 may be connected to the shell 5200. The plurality of cooling assemblies may be configured to cool different regions (or portions) of the detector assembly. For example, the detector module 510 may include three cooling assemblies. One of the three cooling assemblies may be configured to cool detector components in the central region of the detector assembly. The remaining two cooling assemblies may be configured to cool detector components in the ends of the detector assembly.

Figure 8:
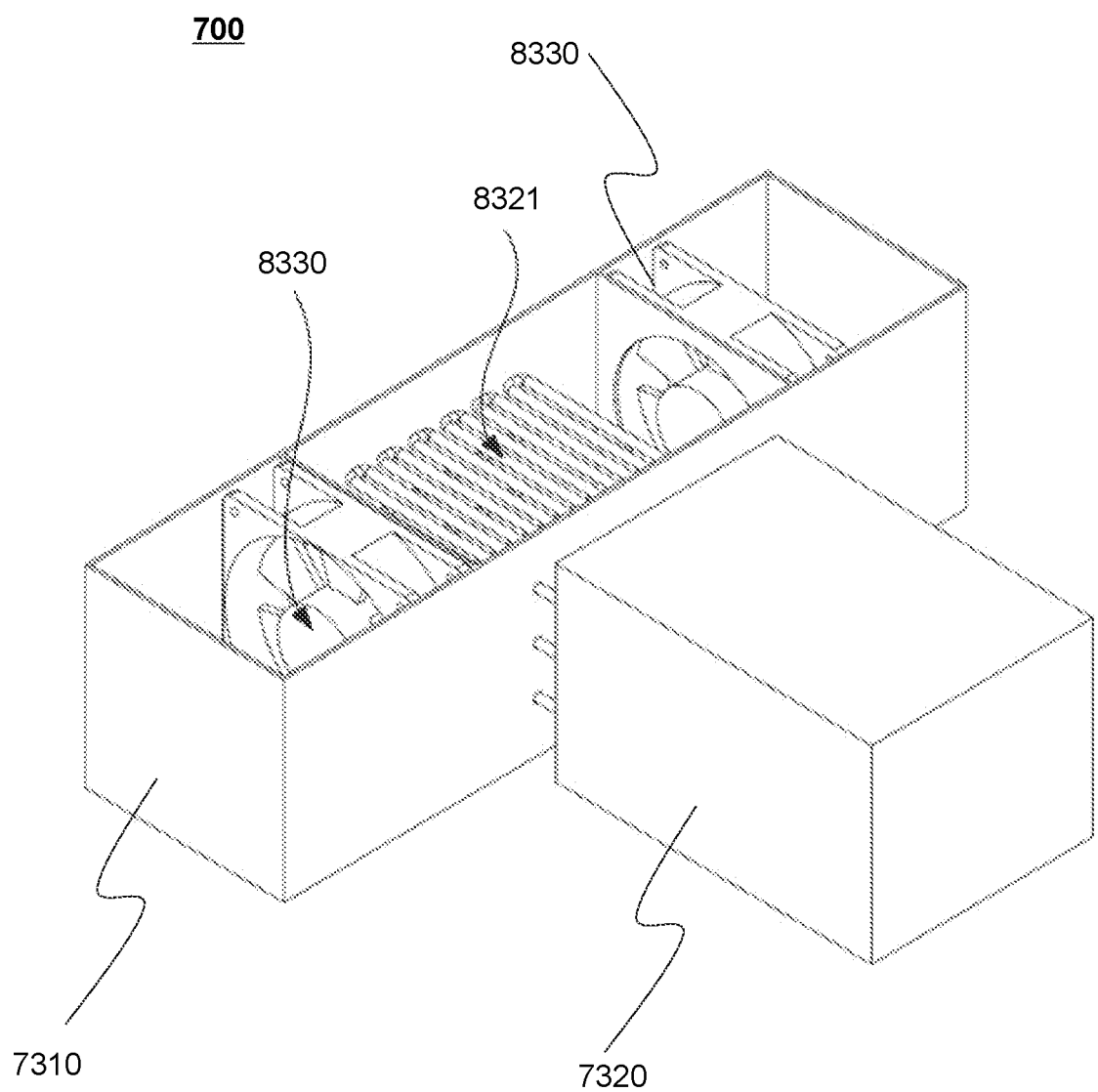

FIGS. 7-8 illustrate an exemplary cooling assembly according to some embodiments of the present disclosure. The cooling assembly 700 may be an example of the cooling assembly 230, and/or the cooling assembly 5300 as illustrated in FIGS. 5A-6B. The cooling assembly 700 may include a cover 7310 and a refrigeration circuit 7320 (also referred to as a cooling component). The refrigeration circuit 7320 may be configured to provide or generate a cooling medium. The cover 7310 may include a second gas inlet 7311 and a second gas outlet 7312. The cooling medium may flow between a cover assembly (e.g., the cover assembly as illustrated in FIGS. 2, 5A-6B) and the cooling assembly 700 through the second gas inlet 7311 and the second gas outlet 7312.

Specifically, the refrigeration circuit 7320 may include an evaporator 8321 configured to provide or generate the cooling medium. As illustrated in FIG. 8, the evaporator 8321 may be located inside the cover 7310. The refrigeration circuit 7320 may also include two fans 8330. In some embodiments, as illustrated in FIG. 8, the two fans 8330 may be located inside the cover 7310. The two fans 8330 may be configured to regulate or accelerate a flow rate of the cooling medium (e.g., a gas) flowing between the cover assembly and the cooling assembly 700. In some embodiments, the evaporator 8321 may be located between the two fans 8330.

The two fans 8330 may be set near to the second gas inlet 7311 and second gas outlet 7312, respectively. By arranging the two fans 8330 near to the evaporator 8321, the second gas inlet 7311 and second gas outlet 7312, and the two fans 8330 may efficiently regulate or accelerate the flow rate of the gas flowing between the cover assembly and the cooling assembly 700.

Figure 10:
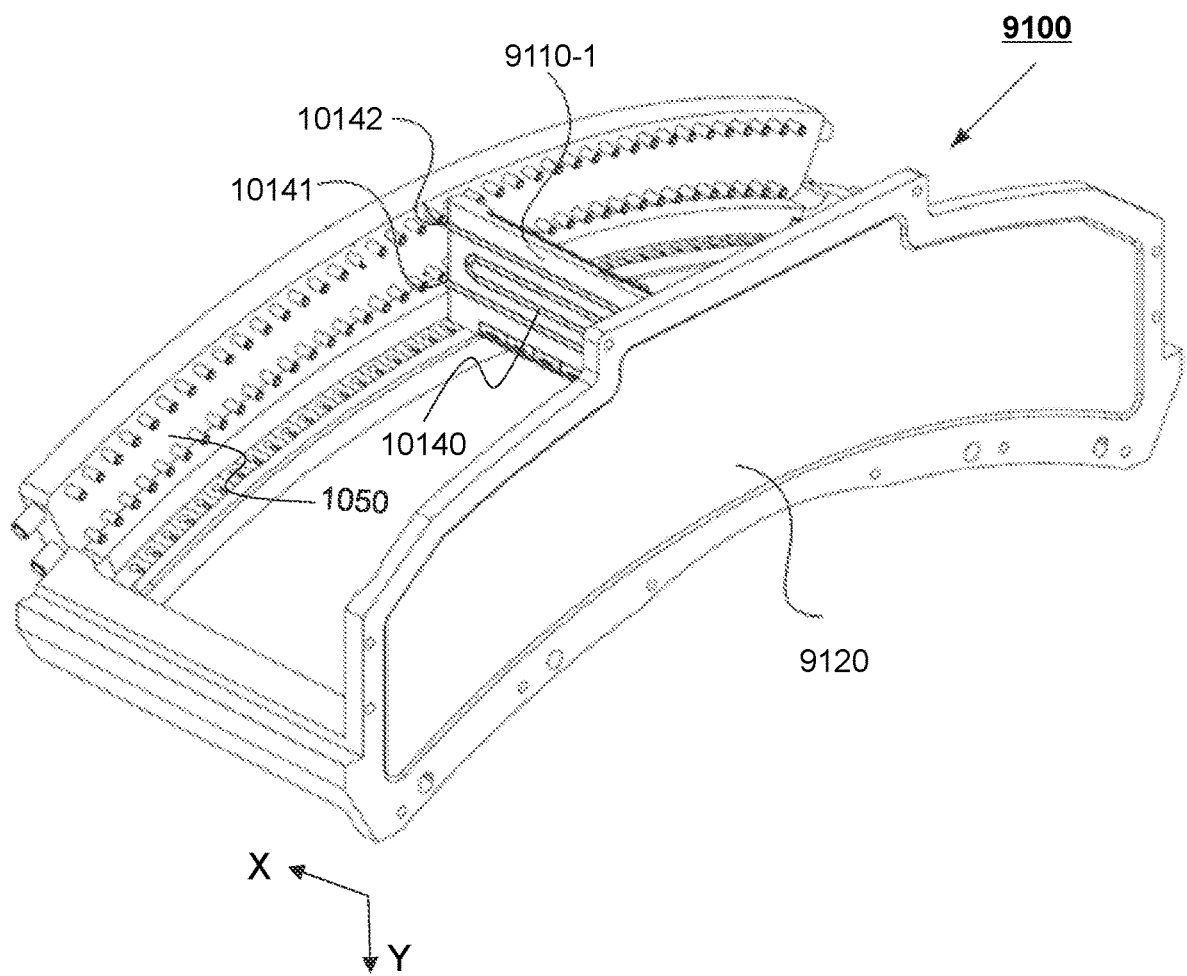

FIGS. 9-10 illustrate different views of an exemplary detector module according to some embodiments of the present disclosure.

The detector module 9100 may include a cover assembly, a plurality of detector components 9110 (collectively referred to as a "detector assembly"), a plurality of pipes, and a medium separation component 9130. A detector component 9110-1 as illustrated in FIG. 10 may be an exemplary detector component. A pipe 10140 as illustrated in FIG. 10 may be an exemplary pipe. Similar to the detector assembly as illustrated in FIGS. 5A-6B, the detector assembly in FIGS. 9-10 may be configured to detect signal(s) associated with an object, e.g., attenuated radioactive rays (e.g., X rays), radiation events (e.g., gamma photons), etc. Taking a CT apparatus as an example, the detector assembly may receive attenuated X-rays passing through the object and detect signal(s) thereof and process the signal(s). The detector assembly may also process and/or transmit the signal(s) to other components of the imaging system 100 for image reconstruction.

The detector assembly may be accommodated in the cover assembly. Similar to the cover assembly as illustrated in FIG. 5A-6B, the cover assembly may include a chamber configured to accommodate and/or enclose the detector assembly. In some embodiments, the cover assembly may include a support component 9120 and a shell (not shown in FIG. 9). The support component 9120 and the shell may be connected to each other and form the chamber. In some embodiments, the support component 9120 and the shell may form the chamber to accommodate and/or enclose the detector assembly. In some embodiments, the shapes of a cross section of the support component 9120 and a cross section of the shell may be mutually fitted to form the chamber. For example, cross sections of the support component 9120 and the shell may have an arcuate shape, a square shape, a trapezoid shape, etc.

Similar to the support component 5100 as illustrated in FIGS. 5A-6B, the support component 9120 may be used as a base for mounting the detector assembly. The shell may be operably coupled to the support component 9120. For example, the detector assembly may be mounted on the support component 9120 by welding, embedding, through one or more mechanical fasteners (e.g., a bolt, a screw, a nut, a gasket, an airtight glue, an airtight adhesive tape), or the like, or a combination thereof. It should be noted the support component 9120 and the shell may be used interchangeably. As illustrated in FIGS. 9-10, the detector components 9110 may be mounted on the support component 9120. In some alternative embodiments, the detector components 9110 may be mounted on the shell.

In some embodiments, the support component 9120 and/or the shell may include one or more plates. For illustration purposes, the support component 9120 may include a first side plate and a bottom plate. The side plate may cover or support a first side (e.g., a side in the negative X-axis direction of the detector components 9110) of the detector module 9100. The bottom plate may cover or support the bottom surface of the detector module 9100 (e.g., the surface of the detector module 9100 facing the object). In some embodiments, the first side plate and the bottom plate may be configured as an integral piece or two pieces connected with each other. For illustration purposes, the shell may include a second side plate and an upper plate. The second side plate may cover a second side (e.g., a side in the positive X-axis direction of the detector components 9110) of the detector module 9100. The upper plate may cover the upper surface of the detector module 9100 (e.g., the surface of the detector module 9100 opposite to the object). In some embodiments, the second side plate and the upper plate may be configured as an integral piece or two pieces connected with each other.

The detector components 9110 may be arranged inside the chamber along a length direction (e.g., a circumferential direction, or a rotation direction) of the cover assembly. As shown in FIG. 9, the orientation of each of the detector components 9110 may be parallel (or substantially parallel) to a width direction (e.g., the X-axis direction as illustrated in FIG. 9) of the cover assembly (e.g., the support component 9120). Specifically, a length direction of each of the detector components 9110 may extend along a width direction of the cover assembly. A width direction of each of the plurality of detector components may extend along the length direction of the cover assembly. In some embodiments, a length direction and a width direction of the detector assembly may be different from the length direction and the width direction of each detector component, respectively. For illustration purposes, the length direction of the detector assembly may extend along the length direction of the cover assembly. The width direction of the detector assembly may extend along the width direction of the cover assembly.

In some embodiments, when the detector assembly implements functions, e.g., receiving the attenuated rays, detecting, processing and/or transmitting the signal(s), the detector assembly may generate a great amount of heat. If the heat is accumulated to a certain extent, the detector assembly may fail to function properly and the signal(s) may become inaccurate, thereby affecting the accuracy of the image(s) reconstructed based on the inaccurate signal(s). In order to solve the problem, it may be necessary to cool the detector components 9110. As illustrated in FIG. 10, the detector component 9110-1 may be equipped with (or coupled with) one or more pipes 10140. A cooling medium (e.g., water, oil) may flow into the pipe(s) 10140, absorb at least a portion of the heat generated by the detector component 9110-1, and cool the detector component 9110-1. In some embodiments, the detector module 9100 may include a plurality of pipes. Each of the plurality of pipes may be the same as or similar to the pipe 10140. In some embodiments, each of the detector components 9110 may be equipped with at least one of the plurality of pipes. In some embodiments, the number (or count) of the plurality of pipes may be the same as the number (or count) of the detector components 9110. In some embodiments, the number (or count) of the plurality of pipes may be different from the number (or count) of the detector components 9110. For example, two detector components may share one of the plurality of pipes located between the two detector components. In some embodiments, the cooling medium flowing in the plurality of pipes may cool the detector assembly so that the temperatures of different portions of the detector assembly may be maintained at an acceptable temperature level and the detector assembly may function properly, thereby guaranteeing the quality of the reconstructed image(s).

In some embodiments, the detector components 9110 may be spaced with each other inside the chamber. For example, two adjacent detector components may include a gap therebetween. A portion of the heat generated by the detector components 9110 may dissipate towards the gap, thereby avoiding heat concentration (or overheating) in the detector components 9110. In some embodiments, the cooling medium in the pipes may absorb heat in the gap(s) and cool the gas in the gap(s), and improve the cooling effect of the detector components 9110. In some embodiments, the pipe(s) may be filled with a first cooling medium (e.g., a cooling liquid), and the gap(s) between adjacent detector components may be filled with a second cooling medium (e.g., a cooling gas as illustrated in FIGS. 5A-6B). In some embodiments, the detector module 9100 may further include a structure of the detector module 510 shown in FIGS. 5A-6B. In some embodiments, the cooling assembly 5300 may provide a cooling gas to the gap(s) between adjacent detector components of the detector components 9110. In some embodiments, the cooling medium in the pipes and the cooling gas (e.g., provided by the cooling assembly 5300 in FIGS. 5A-6B) in the gap(s) may quickly cool the detector components 9110 and improve the performance of the detector components 9110.

As illustrated in FIG. 10, the pipe 10140 may include an inlet port 10141 and an outlet port 10142. The cooling medium may flow from the inlet port 10141 into the pipe 10140 and flow out of the pipe 10421 from the outlet port 10142. Specifically, the cooling medium may flow into the pipe 10140 via the inlet port 10141 and absorb a portion of the heat of the detector component 9110-1. Then the heat-laden cooling medium may flow out of the pipe 10140 via the outlet port 10142. This process may be repeated to cool the detector component 9110-1. Finally, the temperatures of detector components 9110 in different regions of the detector assembly may maintain at an acceptable temperature level. Further, the temperature of the chamber may maintain at an acceptable temperature level. More descriptions of the detector components 9110 may be found elsewhere in the present disclosure, (e.g., FIGS. 11-12 and the descriptions thereof).

In some embodiments, the medium separation component 9130 may be mounted on the cover assembly (e.g., the support component 9120) and operably coupled to the plurality of pipes. The medium separation component 9130 may be configured to distribute the cooling medium into the plurality of pipes. For example, the cooling medium may include a cooling liquid, e.g., cooling water, cooling oil, etc. Each of the plurality of pipes may be configured to guide a portion of the cooling medium to flow through a corresponding detector component of the detector components 9110.

In some embodiments, the medium separation component 9130 may continuously distribute the cooling medium into the pipe(s) 10140. The cooling medium may promptly absorb the heat generated by the detector components 9110. In some embodiments, the plurality of pipes may be independent or separated from each other and disconnected with each other. Each of the detector components 9110 may be cooled by the cooling medium flowing in a corresponding pipe. Specifically, the cooling medium may simultaneously (almost simultaneously) absorb heat generated by each of the detector components 9110, thereby evenly cooling the detector components 9110 and avoiding overheating and/or a temperature gradient in different positions of the detector assembly.

In some embodiments, the medium separation component 9130 may include one or more medium separation sub-components. Each of the medium separation sub-component(s) may be operably coupled to at least a portion of the plurality of pipes. In some embodiments, the medium separation sub-component(s) may be independent or separated from each other and disconnected with each other. Each of the medium separation sub-component(s) may be configured to independently distribute a portion of the cooling medium to the at least a portion of the plurality of pipes. In some embodiments, each of the medium separation sub-component(s) may include or be coupled to a chamber (e.g., a liquid chamber) configured to store the cooling medium. The chamber may be inside each medium separation sub-component or an external chamber. The chamber of each of the medium separation sub-component(s) may be independent or separated from each other and disconnected with each other. For example, the cooling medium inside a first chamber of a first medium separation sub-component may be not in fluid communication with the cooling medium inside a second chamber of a second medium separation sub-component. In some embodiments, one or more parameters associated with each medium separation sub-component may be controlled independently. Exemplary parameters may include the working state of a medium separation sub-component, a chamber of a cooling medium of a medium separation sub-component, the flow rate of a cooling medium of a medium separation sub-component (e.g., a corresponding main medium inlet, a corresponding main medium outlet, a corresponding branch medium inlet or a corresponding branch medium outlet), the amount of a cooling medium of a medium separation sub-component, or the like, or any combination thereof. For illustration purposes, the medium separation sub-component(s) may include a first medium separation sub-component, a second medium separation sub-component, and a third medium separation sub-component. The first medium separation sub-component may be configured to independently distribute a first portion of the cooling medium to a first portion of the plurality of pipes. The second medium separation sub-component may be configured to independently distribute a second portion of the cooling medium to a second portion of the plurality of pipes. The third medium separation sub-component may be configured to independently distribute a third portion of the cooling medium to a third portion of the plurality of pipes (e.g., the remaining pipes).

For two detector components that have a certain distance, e.g., a first detector component and a second detector component, if the cooling medium is directly delivered from the first detector component to the second detector component, the second detector component may be cooled more slowly than the first detector component, thereby causing a temperature gradient in different positions of the detector assembly. By coupling two or more independent and/or disconnected medium separation sub-components to two or more detector components in different portions (or regions) of the detector assembly, respectively, detector components in different regions may be cooled by cooling mediums delivered by different medium separation sub-components at the same (or substantially the same) time. The entire detector assembly may be cooled quickly and evenly. In some embodiments, the medium separation sub-component(s) may be made of a material including, e.g., a thermal insulation material, to prevent or reduce heat exchange between different medium separation sub-components. Exemplary thermal insulation materials may include insulated cotton, ceramics, insulated plastic, or the like, or any combination thereof.

In some embodiments, each of the medium separation sub-component(s) may include a main medium inlet, a main medium outlet, one or more branch medium inlets, and/or one or more branch medium outlets. The cooling medium may flow from a corresponding chamber into a corresponding main medium inlet or from a corresponding main medium outlet into the corresponding chamber. The cooling medium may be capable of flowing from the main medium inlet to the one or more branch medium outlets or from the one or more branch medium inlets to the main medium outlet. In some embodiments, each branch medium outlet may be operably coupled to an inlet port of one of the plurality of pipes. In some embodiments, each branch medium inlet may be operably coupled to an outlet port of one of the plurality of pipes.

For illustration purposes, the cooling medium may flow from the corresponding chamber into the corresponding main medium inlet. The cooling medium may flow from the main medium inlet to the branch medium outlets, flow from the branch medium outlets to corresponding pipes via the inlet ports of the corresponding pipes, and cool the corresponding detector component(s). The heat-laden cooling medium may then flow out of the pipes via the outlet ports of the pipes to corresponding branch medium inlets, flow from the branch medium inlets via the main medium outlet into the corresponding chamber to be cooled for reuse. This process may be repeated to cool the detector assembly. Finally, the temperatures of different regions of the entire detector assembly may maintain at an acceptable temperature level. Further, the temperature of a chamber formed by a cover assembly may maintain at an acceptable temperature level. In some embodiments, the cooling medium flowing in the plurality of pipes may cool the detector assembly at the same (or substantially the same) time, so that the temperatures of various portions (or regions) of the detector assembly may be maintained at an acceptable temperature level, and the detector assembly may function properly, thereby guaranteeing the quality of the reconstructed image(s).

In some embodiments, the medium separation component 9130 may include at least one flow regulating component. The at least one flow regulating component may be configured to regulate at least one flow rate of the cooling medium flowing through at least a portion of the pipes, thereby regulating the temperature of corresponding detector components. In some embodiments, at least one of the medium separation sub-component(s) may be equipped with one flow regulating component. In some embodiments, each branch medium inlet of the at least one medium separation sub-component may be equipped with one flow regulating component.

In some embodiments, the opening size of each branch medium outlet may be designed to regulate the flow rate of a corresponding pipe connected to the branch medium outlet. For example, the greater the opening size of each branch medium outlet is, the greater the flow rate of the corresponding pipe may be. For a medium separation sub-component, the cooling effect of the cooling medium flowing through a first branch medium outlet near to or close or near to a corresponding main medium inlet may be better than the cooling effect of the cooling medium flowing through a second branch medium outlet far from the corresponding main medium inlet. A first opening size of the first branch medium outlet may be designed to be less than a second opening size of the second branch medium outlet. A second flow rate of the cooling medium in a second pipe corresponding to the second branch medium outlet may be greater than a first flow rate of the cooling medium in a first pipe corresponding to the first branch medium outlet, thereby increasing the cooling effect of the cooling medium flowing through the second pipe, and evenly cooling the detector components 9110.

In some cases, one or more detector components at a central region of the detector assembly may generate more heat than one or more detector components close to the end(s) (or at end regions) of the detector assembly. More descriptions of the central region and the end region(s) may be found elsewhere in the present disclosure (e.g., FIGS. 5A-6B and descriptions thereof). For example, the detector assembly may be evenly and sequentially divided into three regions, i.e., a first region, a second region, and a third region. The second region may be referred to as the central region.

In order to further evenly cool the detector assembly, at least one of the medium separation sub-component(s) may be located at or operably coupled to the central region of the detector assembly. In some embodiments, the amount or flow rate of the cooling medium passing through the detector components at the central region may be regulated to be greater than the amount or flow rate of the cooling medium passing through the detector components at the end region(s) of the detector assembly. In some embodiments, one or more parameters associated with the medium separation sub-component(s) may be designed. Exemplary parameters may include the number (or count) of branch medium inlets or branch medium outlets of a medium separation sub-component, an opening size of a main medium inlet, a main medium outlet, a branch medium inlet or a branch medium outlet, a flow rate of a cooling medium flowing through a pipe, or the like, or any combination thereof. In some embodiments, a first count of the branch medium inlets or branch medium outlets of the medium separation sub-component(s) (located at or operably coupled to the central region of the detector assembly) may be smaller than or equal to a second count of the branch medium inlets or branch medium outlets of each of the other medium separation sub-component(s). In some embodiments, an average flow rate of the cooling medium flowing through the pipes coupled to the medium separation sub-component(s) (located at or operably coupled to the central region of the detector assembly) may be greater than or equal to an average flow rate of the cooling medium flowing through the pipes coupled to another medium separation sub-component. In some embodiments, an average opening size of the pipes coupled to the medium separation sub-component(s) (located at or operably coupled to the central region of the detector assembly) may be greater than or equal to an average opening size of the pipes coupled to other medium separation sub-component(s).

Figure 13:
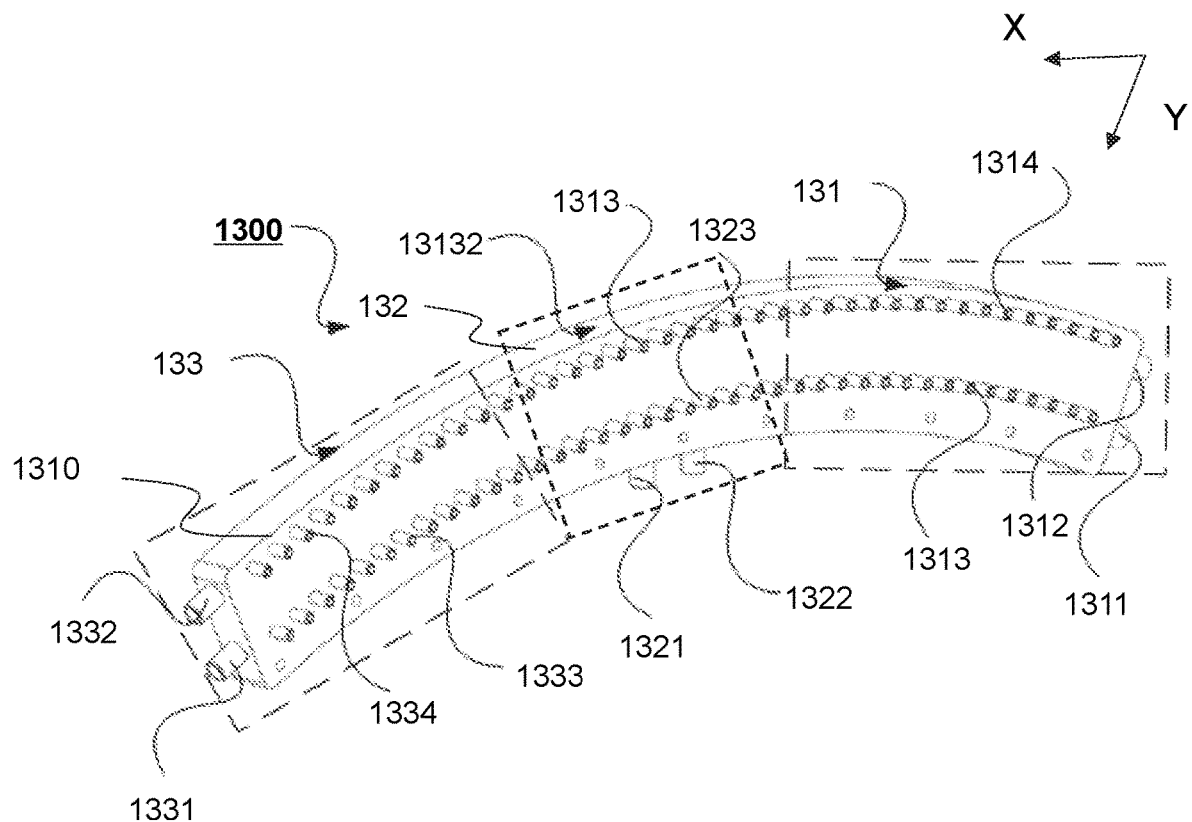
FIG. 13 illustrates an exemplary medium separation component according to some embodiments of the present disclosure.

In some embodiments, a medium separation sub-component may include or be configured as a medium separation plate 1050. The main medium inlet, the main medium outlet, the branch medium inlet(s), and the branch medium outlet(s) of a medium separation sub-component may be arranged at (or disposed on) the medium separation plate 1050. As illustrated in FIGS. 9-10, the medium separation plate 1050 may be in parallel with a sidewall of the support component 9120. In some embodiments, main medium inlets and main medium outlets of different medium separation sub-components may be located at the same side of the medium separation plate 1050. In some embodiments, as illustrated in FIG. 13, the main medium inlets (e.g., a main medium inlet 1311, a main medium inlet 1321, a main medium inlet 1331) and main medium outlets (e.g., a main medium outlet 1312, a main medium outlet 1322, a main medium outlet 1332) of the different medium separation sub-components may be located at different sides of a medium separation plate 1310. In some embodiments, as illustrated in FIG. 13, two or more medium separation sub-components may share the same medium separation plate 1310. In some embodiments, inlet ports of the plurality of pipes, outlet ports of the plurality of pipes, and/or the branch medium inlet(s) and the branch medium outlet(s) of one or more medium separation sub-components may be arranged at the same side facing the same medium separation plate.

In some embodiments, each medium separation sub-component may include a first medium separation plate and a second medium separation plate. The main medium inlet and the branch medium outlet(s) may be arranged on the first medium separation plate. The main medium outlet and the branch medium inlet(s) may be arranged on the second medium separation plate. In some embodiments, two or more medium separation sub-components may share the same first separation plate and the same second separation plate. The main medium inlets and the branch medium outlets of the medium separation sub-components may be arranged on the same first medium separation plate. The main medium outlets and the branch medium inlets of the medium separation sub-components may be arranged on the same second medium separation plate. In some embodiments, the inlet ports of the plurality of pipes may be set facing the first medium separation plate, while the outlet ports of the plurality of pipes may be set facing the second medium separation plate.

In some embodiments, the cover assembly may have or form a sealed structure, thereby protecting components (e.g., the detector assembly) inside the cover assembly from dust and dirt or being collided by a component external to the cover assembly. Therefore, the service life, the stability, and/or work efficiency of the detector module 9100 may be improved. In some embodiments, for a CT apparatus, the detector module 9100 may be attached to or fixed on a frame assembly (e.g., a rotary frame) of the CT apparatus through the cover assembly (e.g., the support component 9120). In some embodiments, the cover assembly may be made of a heat-conductive material (e.g., a metallic material, or the like), thereby conducting a portion of the heat generated by the detector assembly to other components of the detector module 9100, and further facilitating the cooling of the detector assembly.

It should be noted the number (or count) of medium separation sub-component(s) may be non-limiting, and be set according to practical needs, e.g., the amount of heat generated by the detector assembly, the duration and/or frequency of using the detector assembly, the time for cooling the detector assembly, etc. For illustration purposes, the number (or count) of the medium separation sub-component(s) (located at or operably coupled to the central region of the detector assembly) may include 1, 2, 3 or more.

In some embodiments, the detector module 9110 may further include one or more other cooling assemblies. In some embodiments, the structure of the cooling assemblies may be the same as or similar to the cooling assembly as illustrated in FIGS. 2, 5A-6B, and relevant descriptions are not repeated here.

Figure 12:
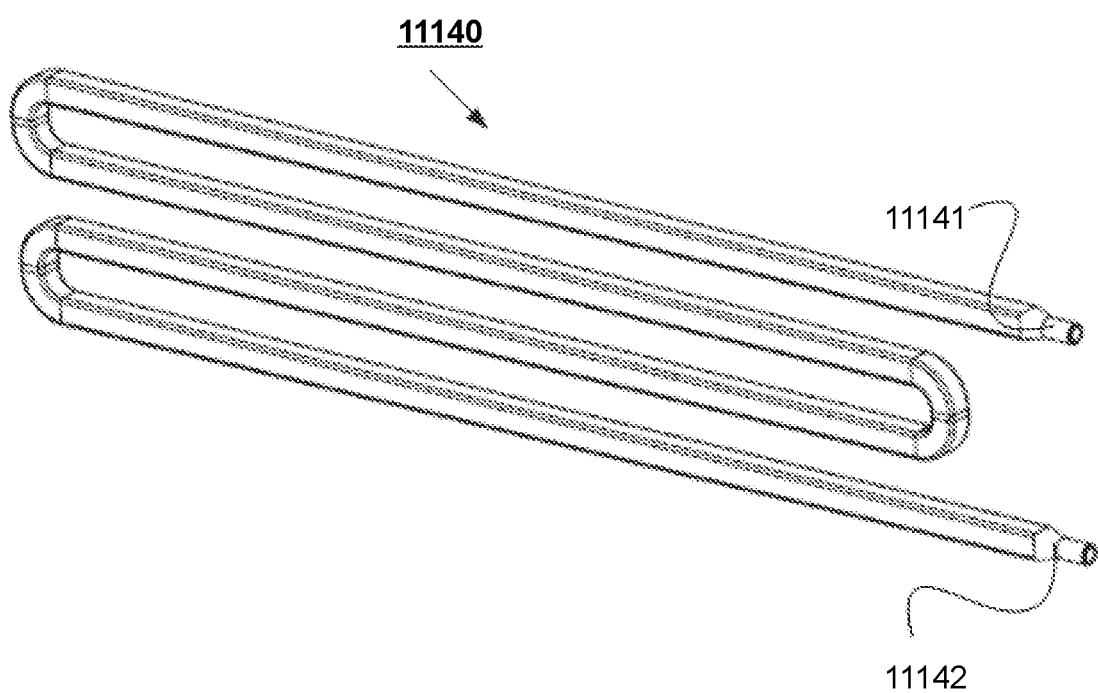
FIG. 12 illustrates an exemplary pipe of a detector component according to some embodiments of the present disclosure.

FIG. 11 illustrates an exemplary detector component according to some embodiments of the present disclosure. FIG. 12 illustrates an exemplary pipe of the detector component illustrated in FIG. 11 according to some embodiments of the present disclosure. The detector component 1100 may be an exemplary detector component as illustrated in FIGS. 2, 5A-10.

As illustrated in FIG. 11, the detector component 1100 may include an electronic component 11111, a frame 11112, and a pipe 11140. For illustration purposes, a cross section (e.g., in the XY plane) of the pipe 10140 may have a square shape, a trapezoid shape, etc. The electronic component 11111 may be configured to detect signal(s) associated with an object (e.g., a patient). Taking a CT apparatus as an example, the electronic component 11111 may receive attenuated X-rays passing through the object and detect signal(s) thereof and/or process the signal(s). In some embodiments, the electronic component 11111 may process and/or transmit the signal(s) to other components of the imaging system 100 for image reconstruction.

In some embodiments, the electronic component 11111 may include a detector unit, a signal transmission board, and/or a signal processing board. The detector unit may be configured to receive the attenuated X-rays and detect the signal(s) thereof. The signal transmission board may be electrically coupled to the detector unit and/or the signal processing board. The signal transmission board may transmit the signal(s) to the signal processing board. The signal processing board may be configured to process the signal(s).

In some embodiments, when the electronic component 11111 implements functions, e.g., receiving the attenuated rays, detecting, processing and/or transmitting the signal(s), the electronic component 11111 may generate a great amount of heat. If the heat is accumulated to a certain extent, the electronic component 11111 may fail to function properly and the signal(s) may become inaccurate, thereby affecting the accuracy of the image(s) reconstructed based on the inaccurate signal(s). In order to solve the problem, it may be necessary to cool the electronic component 11111. As illustrated in FIG. 11, the frame 11112 may be equipped with at least one pipe 11140. A cooling medium may flow into the pipe 11140 (e.g., via an inlet port 11141 of the pipe 11140), absorb at least a portion of the heat, and cool the electronic component 11111. As illustrated in FIGS. 9-10, the medium separation component 9130 may distribute the cooling medium into the pipe(s) 11140. In some embodiments, the medium separation component 9130 may continuously distribute the cooling medium into the pipe(s) 11140. The cooling medium may promptly absorb the heat. More descriptions of the distribution of the cooling medium into the pipe(s) 11140 may be found elsewhere in the present disclosure (e.g., FIGS. 9-10 and the descriptions thereof).

As illustrated in FIG. 11, the frame 11112 may be configured to support the electronic component 11111 (e.g., the detector unit, the signal transmission board, the signal processing board). In some embodiments, a portion of the heat generated by the electronic component 11111 may transfer from the electronic component 11111 to the frame 11112. The cooling medium flowing in the pipe 11140 may absorb at least a portion of the heat and cool the electronic component 11111. Further, the temperature of the entire detector component 1100 may maintain at an acceptable level, without affecting the accuracy of detecting the signal(s) and/or processing the signal(s), thereby ensuring the quality of the reconstructed image(s). In some embodiments, the frame 11112 may be made of a heat-conductive material (e.g., a metallic material, or the like) that can conduct a portion of the heat generated by the detector component 1100 to the frame 11112. In some alternative embodiments, the frame 11112 may be made of a non-conductive material.

The pipe 11140 may include an inlet port 11141 and an outlet port 11142. The pipe 11140 (e.g., the mounting position of the pipe 11140, the shape of the pipe 11140, the mounting mode of the pipe 11140, etc.) may be designed to efficiently cool the entire detector component 1100. In some embodiments, the mounting position of the pipe 11140 may be designed to efficiently cool the entire detector component 1100. In some embodiments, the pipe 11140 may be located at a central region of the frame 11112. Additionally or alternatively, the pipe 11140 may extend along a length direction (e.g., the X-axis direction as illustrated in FIG. 11)) of the frame 11112 or a length direction of the electronic component 11111 (e.g., the X-axis direction as illustrated in FIG. 11). Thus the cooling medium may efficiently absorb the heat.

As illustrated in FIG. 11, the inlet port 11141 and the outlet port 11142 may be located at different positions along a height direction (e.g., the Y-axis direction as illustrated in FIG. 11) of the frame 11112 or a height direction of the electronic component 11111 (e.g., the Y-axis direction as illustrated in FIG. 11). In some embodiments, the inlet port 11141 of the pipe 11140 may be located closer to the electronic component 11111 than the outlet port 11142 of the pipe 11140 in the height direction of the frame 11112. In some embodiments, the inlet port 11141 may be located at a higher position ((e.g., a position in the negative Y-axis direction as illustrated in FIG. 11) along the height direction of the frame 11112 than the outlet port 11142. Because the heat may be generated by the electronic component 11111 and a portion of the heat may dissipate to the frame 11112, the temperature of a higher part (e.g., a part of the frame 11112 in the negative Y-axis direction as illustrated in FIG. 11) of the frame 11112 may be higher than the temperature of a lower part (e.g., a part of the frame 11112 in the positive Y-axis direction as illustrated in FIG. 11) of the frame 11112. As illustrated above, the cooling medium may flow from the inlet port 11141 into the pipe 11140. The cooling medium may absorb at least a portion of the heat, and then flow out of the pipe 11140 into the outlet port 11142. Because the temperature of the higher part of the frame 11112 may be higher than the temperature of the lower part of the frame 11112, the inlet port 11141 may be located at the higher position to cause the cooling medium to quickly cool the higher part of the frame 11112 and the electronic component 11111, and then cool the lower part of the frame 11112. The entire detector component 1100 may be cooled evenly, thereby ensuring the accuracy of the detected signal(s), the processed signal(s), and the quality of the reconstructed image(s).

In some embodiments, the shape of the pipe 11140 may be designed to efficiently cool the entire detector component 1100. In some embodiments, the pipe 11140 may be bent inside (or embedded in) the frame 11112 for one or more times to increase a contact area of the pipe 11140 and the frame 11112. The cooling medium may flow through the contact area and improve the cooling efficiency of the detector component 1100. Besides, portions (or regions) near the contact area of the detector component 1100 and the pipe(s) 11140 may be cooled uniformly to ensure the entire detector component 1100 to be cooled evenly. It should be understood that the number (or count) of bends of the pipe(s) 11140 may be set according to practical needs in cooling the detector component 1100, e.g., the time for cooling the detector component 1100, the amount of heat generated by the detector component 1100. For example, the pipe 11140 may be bent as a U shape.

In some embodiments, the mounting mode of the pipe 11140 may be designed to efficiently cool the entire detector component 1100. In some embodiments, the frame 11112 may include a groove. The pipe 11140 may be mounted (or embedded) in the groove. In some embodiments, the pipe 11140 may be mounted in the groove by welding, embedding, pasting, or through a mechanical fastener. For example, the mechanical fastener may include a bolt, a screw, a nut, a gasket, an airtight glue, an airtight adhesive tape, a clamp, or the like, or any combination thereof. In some embodiments, when the groove in the frame 11112 is formed, the pipe 11140 may be placed into the groove. For example, the pipe 11140 may be fixed in the groove by melting (e.g., solder melting) or welding a metal (e.g., stannum). As another example, the pipe 11140 may be fixed in the groove using at least one clamp. In some embodiments, a surface of the frame 11112 and a surface of the pipe 11140 may form a coplane. For example, a surface of the frame 11112 and a surface of the pipe 11140 along the Z-axis direction may form a coplane.

FIG. 13 illustrates an exemplary medium separation component according to some embodiments of the present disclosure. The medium separation component 1300 may be an example of the medium separation component 9130 as illustrated in FIGS. 9-10.

As illustrated in FIG. 13, the medium separation component 1300 may include three medium separation sub-components, i.e., a first medium separation sub-component 131, a second medium separation sub-component 132, a third medium separation sub-component 133. The three medium separation sub-components may share the same medium separation plate 1310. The three medium separation sub-components may be configured as an integral structure. The second medium separation sub-component 132 may be located between the first medium separation sub-component 131 and the third medium separation sub-component 133. The first medium separation sub-component 131 may be configured to distribute a first portion of a cooling medium to a first portion of a plurality of pipes at a right region of a detector assembly. The second medium separation sub-component 132 may be configured to distribute a second portion of the cooling medium to a second portion of the plurality of pipes at a central region of the detector assembly. The third medium separation sub-component 133 may be configured to independently distribute a third portion of the cooling medium to a third portion of the plurality of pipes at a left region of the detector assembly. It should be noted the terms "left region," "central region," and "right region" used herein may be referred to as three regions sequentially located along the positive X-axis direction of the medium separation component 1300.

Specifically, the first medium separation sub-component 131 may include a main medium inlet 1311, a main medium outlet 1312, a plurality of branch medium inlets 1314, and a plurality of branch medium outlets 1313. The main medium inlet 1311 and the main medium outlet 1312 may be operably coupled to a corresponding chamber (not shown). The branch medium outlets 1313 may be operably coupled to the inlet ports of a plurality of pipes located at the right region of the detector assembly. The branch medium inlets 1314 may be operably coupled to the outlet ports of the plurality of pipes located at the right region of the detector assembly. A cooling medium may flow from the chamber into the main medium inlet 1311. The cooling medium may then flow from the main medium inlet 1311 to a corresponding branch medium outlet 1313, and through a corresponding inlet port into a corresponding pipe and cool a corresponding detector component. The heat-laden cooling medium may then flow out of the pipe from a corresponding outlet port into the chamber via a corresponding branch medium inlet 1314, and the main medium outlet 1312.

Similar to the first medium separation sub-component 131, the second medium separation sub-component 132 may include a main medium inlet 1321, a main medium outlet 1322, a plurality of branch medium inlets 1324, and a plurality of branch medium outlets 1323. The main medium inlet 1321 and the main medium outlet 1322 may be operably coupled to a corresponding chamber. The branch medium outlets 1323 may be operably coupled to the inlet ports of a plurality of pipes located at the central region of the detector assembly. The branch medium inlets 1324 may be operably coupled to the outlet ports of a plurality of pipes located at the central region of the detector assembly. A cooling medium may flow from the main medium inlet 1321 to a corresponding branch medium outlet 1323, and through the chamber into the main medium inlet 1321. The heat-laden cooling medium may then flow from a corresponding inlet port into a corresponding pipe and cool a corresponding detector component and then flow out of the pipe from a corresponding outlet port into the chamber via a corresponding branch medium inlet 1324, and the main medium outlet 1322.

Similar to the first medium separation sub-component 131 and/or the second medium separation sub-component 132, the third medium separation sub-component 133 may include a main medium inlet 1331, a main medium outlet 1332, a plurality of branch medium inlets 1334, and a plurality of branch medium outlets 1333. The main medium inlet 1331 and the main medium outlet 1332 may be operably coupled to a corresponding chamber. The branch medium outlets 1333 may be operably coupled to the inlet ports of a plurality of pipes located at the left region of the detector assembly. The branch medium inlets 1334 may be operably coupled to the outlet ports of a plurality of pipes located at the left region of the detector assembly. A cooling medium may flow from the chamber into the main medium inlet 1331. The cooling medium may then flow from the main medium inlet 1331 to a corresponding branch medium outlet 1333, and through a corresponding inlet port into a corresponding pipe and cool a corresponding detector component. The heat-laden cooling medium may then flow out of the pipe from a corresponding outlet port into the chamber via a corresponding branch medium inlet 1334, and the main medium outlet 1332.

By arranging the three independent and/or disconnected medium separation sub-components, one or more detector components at different portions (or regions) of the detector assembly may be cooled by the cooling medium at the same (or substantially the same) time. Therefore, the entire detector assembly may be cooled quickly and evenly.

Figure 14A:
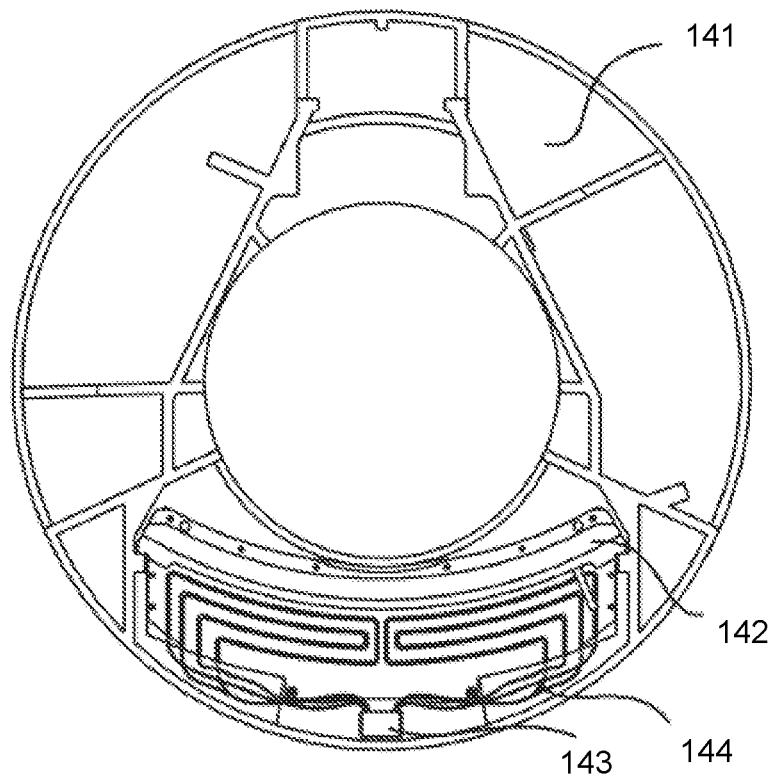
FIG. 14A illustrates a section view of an exemplary scanner according to some embodiments of the present disclosure.
Figure 14B:
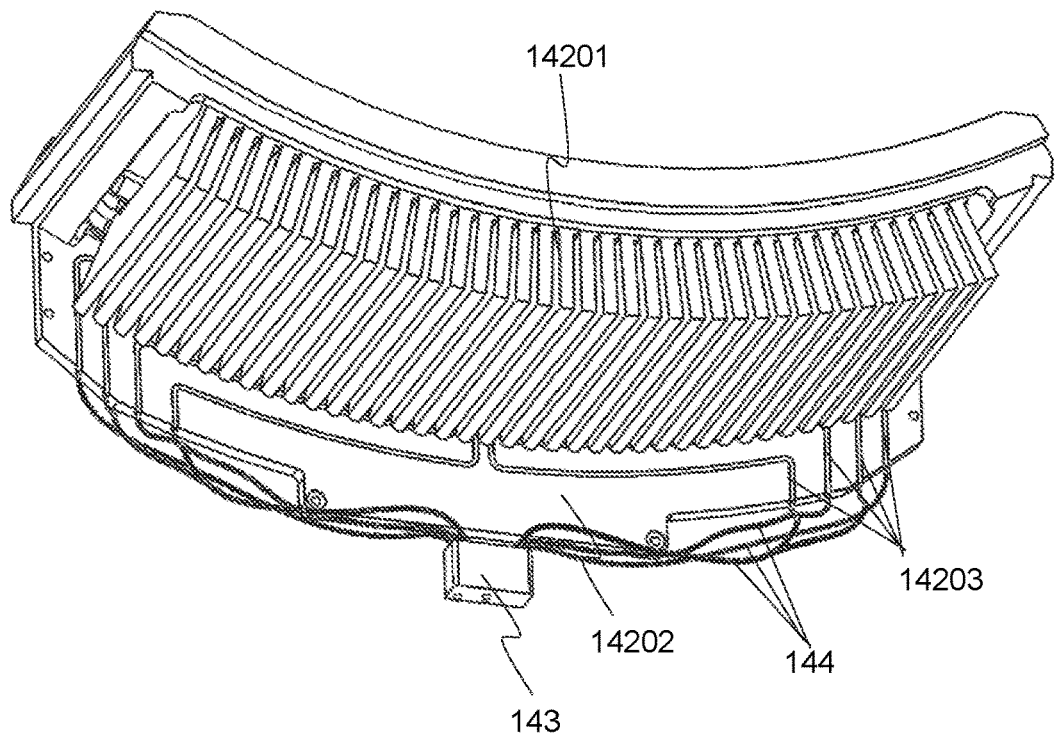
FIGS. 14B-14C illustrate exemplary detector modules according to some embodiments of the present disclosure.
Figure 14C:
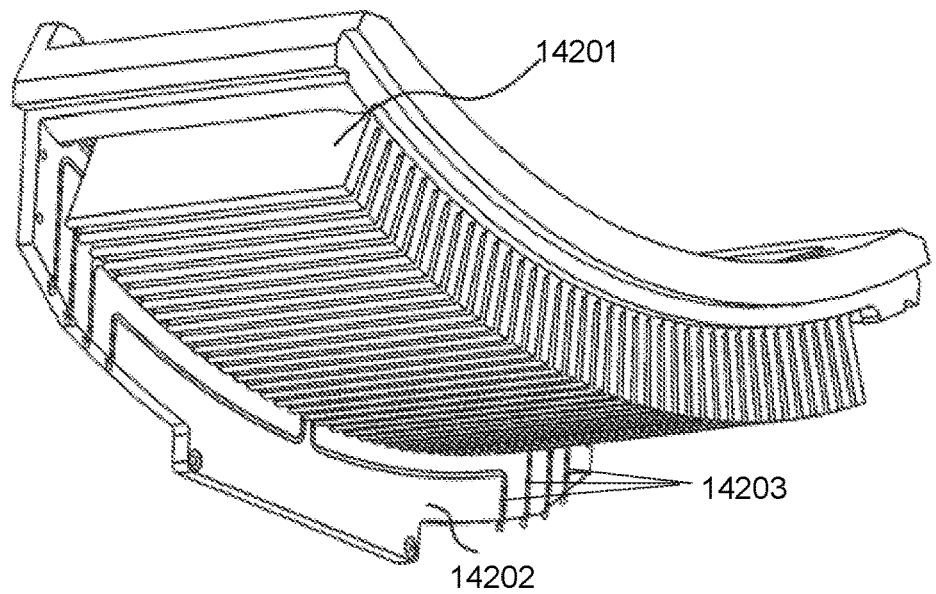

FIG. 14A illustrates a section view of an exemplary scanner according to some embodiments of the present disclosure. FIGS. 14B-14C illustrate exemplary detector modules of the scanner according to some embodiments of the present disclosure. The scanner 1400 may be an example of the scanner 110 as illustrated in FIG. 1. As illustrated in FIG. 14A, the scanner 1400 may include a rotary frame 141 and a detector module 142.

The detector module 142 may be fixed on the rotary frame 141. As illustrated in FIGS. 14B-14C, the detector module 142 may include a plurality of detector components 14201 (collectively referred to as a "detector assembly") and a support component 14202. Similar to the detector assembly as illustrated in FIGS. 5A-6B, and/or the detector assembly as illustrated in FIGS. 9-10, the detector assembly in FIGS. 14B-14C may be configured to detect signal(s) associated with an object, e.g., attenuated radioactive rays (e.g., X rays), radiation events (e.g., gamma photons), etc. Taking a CT apparatus as an example, the detector assembly may receive attenuated X-rays passing through the object and detect signal(s) thereof and process the signal(s). The detector assembly may also process and/or transmit the signal(s) to other components of the imaging system 100 for image reconstruction.

The support component 14202 may be used as a base for mounting the detector assembly. For example, the detector assembly may be mounted on the support component 14202 by welding, embedding, through one or more mechanical fasteners (e.g., a bolt, a screw, a nut, a gasket, an airtight glue, an airtight adhesive tape), or the like, or a combination thereof. In some embodiments, the detector module 142 may also include a shell (not shown). The support component 14202 and the shell (collectively referred to as a "cover assembly") may form a chamber to accommodate and/or enclose the detector assembly. More descriptions of the support component 14202 and the shell may be found elsewhere in the present disclosure (e.g., FIGS. 5-6, 9-10 and the descriptions thereof).

In some embodiments, when the detector assembly implements functions, e.g., receiving the attenuated rays, detecting, processing and/or transmitting the signal(s), the detector assembly may generate a great amount of heat. If the heat is accumulated to a certain extent, the detector assembly may fail to function properly and the signal(s) may become inaccurate, thereby affecting the accuracy of the image(s) reconstructed based on the inaccurate signal(s). In some embodiments, a portion of the heat may dissipate to the support component 14202. Specifically, as illustrated in FIG. 11, each detector assembly may include an electronic component and a frame configured to support the electronic component. The electronic components may implement the functions and generate the heat. A portion of the heat may dissipate to the frame of the detector components, and further dissipate to the support component 14202. In order to solve the problem, it may be necessary to cool the detector assembly and/or the support component 14202. As illustrated in FIGS. 14B-14C, the support component 14202 may be equipped with (or coupled with) a plurality of cooling pipes 14203. A cooling medium (e.g., water, oil) may flow into the cooling pipes 14203, absorb at least a portion of the heat dissipated to the support component 14202, thereby cooling the support component 14202, and further cooling the detector assembly. Similar to the pipe(s) as illustrated in FIGS. 5-6, and 9-10, the support component 14202 may include one or more grooves. The cooling pipes 14203 may be mounted (or embedded) in the one or more grooves. In some embodiments, the cooling pipes 14203 may be mounted in the one or more grooves by welding, embedding, pasting, or through a mechanical fastener. For example, the mechanical fastener may include a bolt, a screw, a nut, a gasket, an airtight glue, an airtight adhesive tape, a clamp, or the like, or any combination thereof. In some embodiments, when the one or more grooves in the support component 14202 are formed, the cooling pipes 14203 may be placed into the one or more grooves. The cooling pipes may be similar to or the same as the pipe(s) as illustrated in FIGS. 5-6, and 9-10, and relevant descriptions are not repeated here.

In some embodiments, the cooling pipes 14203 may be bent inside (or embedded in) the support component 14202 for one or more times so that the cooling medium may circulate inside the cooling pipes 14203. A contact area of the cooling pipes 14203 and the support component 14202 may be increased. The cooling medium may flow through the contact area and improve the cooling efficiency of the support component 14202 and/or the detector assembly. Besides, portions (or regions) near the contact area of the support component 14202 may be cooled uniformly to ensure the detector assembly to be cooled evenly. It should be understood that the number (or count) of bends of the cooling pipes 14203 may be set according to practical needs in cooling the detector assembly, e.g., the time for cooling the detector assembly, the amount of heat generated by the detector assembly.

In some embodiments, the detector module 142 may include at least one medium separation component 143 and a plurality of connection pipes 144. The medium separation component(s) 143 and the connection pipes 144 may be operably coupled to the rotary frame 141, respectively. As illustrated in FIG. 14A, the medium separation component(s) 143 may also be operably coupled to the connection pipes 144. The connection pipes 144 may also be operably coupled to the cooling pipes 14203. The medium separation component(s) 143 may be configured to distribute the cooling medium into the connection pipes 144, and further into the cooling pipes 14203. The connection pipes 144 may be configured to allow the cooling medium to flow between the medium separation component(s) 143 and the cooling pipes 14203. For example, the cooling medium may include a cooling liquid, e.g., cooling water, cooling oil, etc. In some embodiments, the connection pipes 144 and/or the medium separation component(s) 143 may be detached from the detector module 142, e.g., as illustrated in FIG. 14C.

Figure 15A:
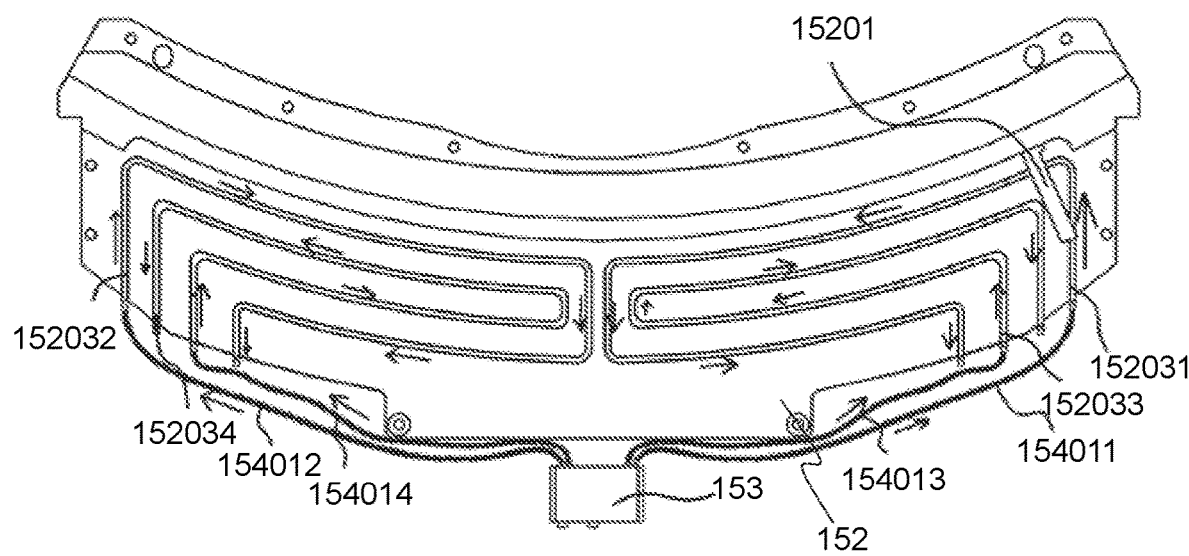
FIGS. 15A-15B illustrate section views of different parts of an exemplary detector module according to some embodiments of the present disclosure.
Figure 15B:
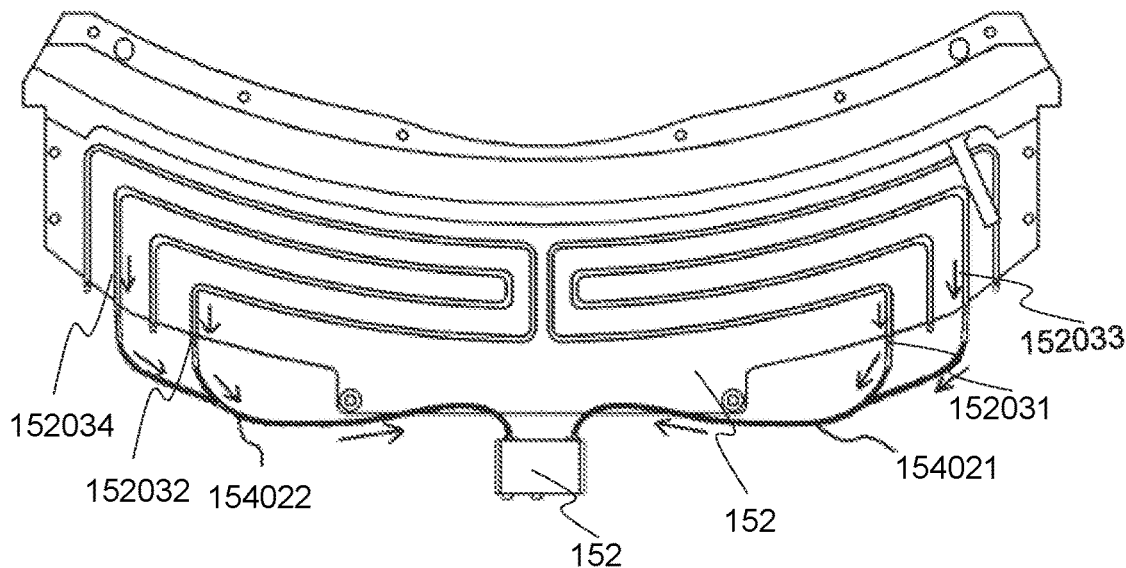

In some embodiments, the connection pipes 144 may include one or more inlet connection pipes and one or more outlet connection pipes. The cooling medium may flow from the medium separation component(s) 143 into the one or more inlet connection pipes, sequentially into the cooling pipes 14203, and absorb the heat from the support component 14202 and/or the detector assembly. Then the heat-laden cooling medium may flow out of the cooling pipes 14203 into the one or more outlet connection pipes. In some embodiments, the heat-laden cooling medium may further flow back to the medium separation component(s) 143. This process may be repeated to cool the support component 14202 and/or the detector assembly. In some embodiments, the number (or count) of the one or more inlet connection pipes and/or the one or more outlet connection pipes may be the same as or different from the cooling pipes 14203. For example, as illustrated in FIGS. 15A-15B, each cooling pipe may be equipped with one of the one or more inlet connection pipes. Two of the cooling pipes 14203 may share the same outlet connection pipe.

In some embodiments, each medium separation component may include a main medium inlet, a main medium outlet, one or more branch medium inlets, and one or more branch medium outlets. The cooling medium may flow from the main medium inlet to the medium separation component(s) 143, and through the one or more branch medium outlets into the one or more inlet connection pipes, and sequentially into the cooling pipes 14203, and absorb the heat from the support component 14202 and/or the detector assembly. Then the heat-laden cooling medium may flow out of the cooling pipes 14203 into the one or more outlet connection pipes. In some embodiments, the heat-laden cooling medium may flow back to the medium separation component through the one or more branch medium inlets. This process may be repeated to cool the support component 14202 and/or the detector assembly. In some embodiments, the medium separation component(s) 143 may be operably coupled to a chamber configured to store the cooling medium. The chamber may be an external chamber to the medium separation component(s) 143.

It should be noted the number (or count) of the branch medium inlet(s) of each medium separation component, the branch medium outlet(s) of each medium separation component, the connection pipes 144, and/or the cooling pipes 14203 may be non-limiting and be set according to practical needs in cooling the detector components, e.g., the time for cooling the detector components, the amount of heat generated by the detector components. For example, the number (or count) of the branch medium inlet(s) of each medium separation component may include 2. The number (or count) of the branch medium outlet(s) of each medium separation component, the connection pipes 144, and/or the cooling pipes 14203 may include 4.

In some embodiments, the medium separation component(s) 143 may continuously distribute the cooling medium into the cooling pipes 14203. The cooling medium may promptly absorb the heat dissipated to the support component 14202 from the detector assembly, thereby cooling the support component 14202, and further cooling the detector assembly. In some embodiments, the cooling pipes 14203 and the connection pipes 144 may be independent or separated from each other and disconnected with each other. Different positions of the support component 14202 and/or detector components at different positions may be cooled by the cooling medium flowing in a corresponding cooling pipe. Specifically, the cooling medium may simultaneously (almost simultaneously) absorb heat generated by different detector components, thereby evenly cooling the detector assembly, and avoiding overheating and/or a temperature gradient in the different positions of the detector assembly.

In some embodiments, the amount and/or the flow rate of the cooling medium flowing through the one or more branch outlets and/or the cooling pipes 14203 may be the same as or different from each other. In some embodiments, the opening size of each branch medium outlet may be designed to regulate the flow rate/amount of the cooling medium of a corresponding cooling pipe and/or a corresponding connection pipe connected to the branch medium outlet, thereby efficiently controlling the temperature inside the detector module 142, and cooling the detector assembly. For example, the greater the opening size of each branch medium outlet is, the greater the flow rate of the corresponding cooling pipe and/or the connection pipe may be. In some cases, one or more detector components at a central region of the detector assembly may generate more heat than one or more detector components close to the end(s) (or at end regions) of the detector assembly. As illustrated above, a portion of the heat generated by the detector assembly may dissipate to the support component 14202. Accordingly, dissipated heat at a central region of the support component 14202 corresponding to the one or more detector components at the central region of the detector assembly may be greater than dissipated heat close to the ends (or at end regions) of the support component 14202 corresponding to the one or more detector components close to the end(s) (or at end regions) of the detector assembly. More descriptions of the central region and the end region(s) may be found elsewhere in the present disclosure (e.g., FIGS. 5A-6B and descriptions thereof). For example, the detector assembly and/or the support component 14202 may be evenly and sequentially divided into three regions, i.e., a first region, a second region, and a third region, respectively. The second region may be referred to as the central region of the detector assembly and/or the support component 14202, respectively.

In order to further evenly cool the detector assembly, at least one of the cooling pipes 14203 may be located at the central region of the support component 14202. In some embodiments, the amount or flow rate of the cooling medium passing through the at least one cooling pipe at the central region of the support component 14202 may be regulated to be greater than the amount or flow rate of the cooling medium passing through at least one cooling pipe at the end region(s) of the support component 14202. For illustration purposes, an average opening size of the at least cooling pipe located at the central region of the support component 14202 may be greater than or equal to an average opening size of the at least one cooling pipe located at the ends of the support component 14202.

It should be noted that the number (or count) of the medium separation component(s) 143 may be non-limiting. In some embodiments, by increasing the number (or count) of the medium separation component(s) 143, the lengths of the connection pipes 144 may be relatively short so that the cooling medium may reach the cooling pipes 14203 in a relatively short time, thereby quickly cooling the support component 14202 and the detector assembly, and avoiding (or reducing, or eliminating) the temperature gradient in different positions of the detector assembly.

In some embodiments, the detector module 142 may further include one or more other cooling assemblies. In some embodiments, the structure of the cooling assemblies may be the same as or similar to the cooling assembly as illustrated in FIGS. 2, 5A-10, and 13 and/or the medium separation component and the pipes as illustrated in FIGS. 10, 13, and relevant descriptions are not repeated here.

Figure 15C:
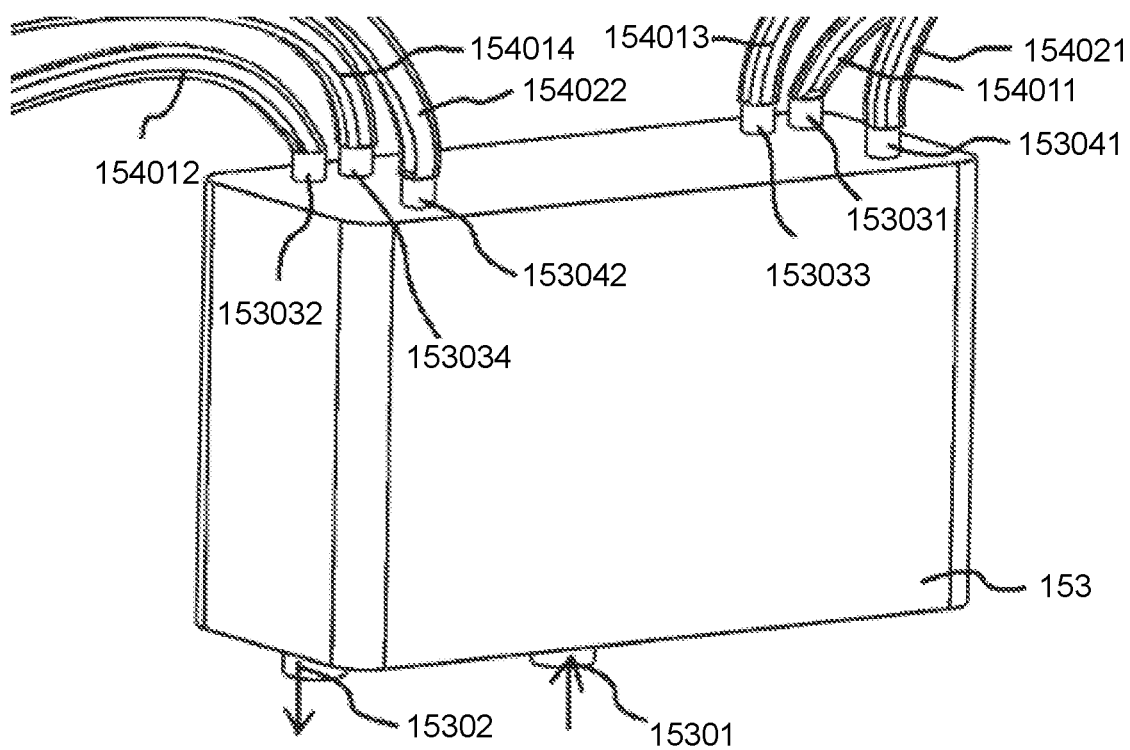
FIG. 15C illustrates an exemplary medium separation component according to some embodiments of the present disclosure.

FIGS. 15A-15B illustrate section views of different parts of an exemplary detector module according to some embodiments of the present disclosure. FIG. 15C illustrates an exemplary medium separation component of the detector module according to some embodiments of the present disclosure. The detector module 1500 may be an example of the detector module 142 as illustrated in FIG. 14.

As illustrated in FIGS. 15A-15B, the detector module 1500 may include a detector component 15201, a support component 152, four cooling pipes, four inlet connection pipes, and two outlet connection pipes. The four cooling pipes may include a first cooling pipe 152031, a second cooling pipe 152032, a third cooling pipe 152033, and a fourth cooling pipe 152034. The four inlet connection pipes may include a first inlet connection pipe 154011, a second inlet connection pipe 154012, a third inlet connection pipe 154013, and a fourth inlet connection pipe 154014. The two outlet connection pipes may include a first outlet connection pipe 154021 and a second outlet connection pipe 154022. Similar to the detector module 142 as illustrated in FIG. 14, the detector module 1500 may include a plurality of detector components. The detector component 15201 may be an exemplary detector component of the plurality of detector components.

As illustrated in FIGS. 15A-15B, the first inlet connection pipe 154011, the second inlet connection pipe 154012, the third inlet connection pipe 154013, and the fourth inlet connection pipe 154014 may be operably coupled to the first cooling pipe 152031, the second cooling pipe 152032, the third cooling pipe 152033, and the fourth cooling pipe 152034. The first cooling pipe 152031 and the third cooling pipe 152033 may be operably coupled to the first outlet connection pipe 154021. The second cooling pipe 152032 and the fourth cooling pipe 152034 may be operably coupled to the second outlet connection pipe 154022.

As indicated by arrows in FIGS. 15A-15B, a cooling medium may flow from the first inlet connection pipe 154011, the second inlet connection pipe 154012, the third inlet connection pipe 154013, and the fourth inlet connection pipe 154014 into the first cooling pipe 152031, the second cooling pipe 152032, the third cooling pipe 152033, and the fourth cooling pipe 152034, respectively. Then the cooling medium (or the heat-laden cooling medium) may flow out of the first cooling pipe 152031 and the third cooling pipe 152033 to the first outlet connection pipe 154021, and/or flow out of the second cooling pipe 152032 and the fourth cooling pipe 152034 to the second outlet connection pipe 154022.

As illustrated in FIG. 16, the medium separation component 153 may also include or be operably coupled to four branch medium outlets, two branch medium inlets, a main medium inlet 15301, and a main medium outlet 15302. As indicated by arrows in FIG. 15C, the cooling medium may flow from the main medium inlet 15301 into the medium separation component 153, and flow out of the medium separation component 153 from the main medium outlet 15302.

The four branch medium outlets may include a first branch medium outlet 153031, a second branch medium outlet 153032, a third branch medium outlet 153033, and a fourth branch medium outlet 153034. The two branch medium inlets may include a first branch medium inlet 153041 and a second branch medium inlet 153042. The first branch medium outlet 153031, the second branch medium outlet 153032, the third branch medium outlet 153033, and the fourth branch medium outlet 153034 may be operably coupled to the first inlet connection pipe 154011, the second inlet connection pipe 154012, the third inlet connection pipe 154013, and the fourth inlet connection pipe 154014. The first branch medium inlet 153041 and the second branch medium inlet 153042 may be operably coupled to the first outlet connection pipe 154021 and the second outlet connection pipe 154022. The cooling medium may flow from the medium separation component 153, through the first branch medium outlet 153031, the second branch medium outlet 153032, the third branch medium outlet 153033, and the fourth branch medium outlet 153034, into the first inlet connection pipe 154011, the second inlet connection pipe 154012, the third inlet connection pipe 154013, and the fourth inlet connection pipe 154014, respectively. The cooling medium (or the heat-laden cooling medium) may flow back to the medium separation component 153, through the first branch medium inlet 153041 and the second branch medium inlet 153042, from the first outlet connection pipe 154021 and the second outlet connection pipe 154022.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A detector module, comprising:
    a detector assembly configured to detect a signal associated with an object;
    a cover assembly configured to accommodate the detector assembly; and
    at least one cooling assembly operably coupled to the cover assembly, wherein the at least one cooling assembly is configured to cool the detector assembly by providing a cooling medium to the cover assembly, wherein
    the cover assembly includes at least one first gas inlet and at least one first gas outlet;
    each of the at least one cooling assembly includes a second gas inlet and a second gas outlet;
    the at least one first gas inlet and the at least one first gas outlet of the cover assembly, and the second gas inlet and the second gas outlet of the each of the at least one cooling assembly are configured to form a fluid communication between the cover assembly and the at least one cooling assembly; and
    the cover assembly and the at least one cooling assembly have or form one or more sealed structures.

2. The detector module of claim 1, wherein each of the at least one first gas inlet and a corresponding first gas outlet of the at least one first gas outlet are arranged along a width direction of the cover assembly.

3. The detector module of claim 1, further comprising a gas inlet chamber located inside the cover assembly, wherein the gas inlet chamber is in fluid communication with the at least one first gas inlet.

4. The detector module of claim 1, further comprising a gas outlet chamber located inside the cover assembly, wherein the gas outlet chamber is in fluid communication with the at least one first gas outlet.

5. The detector module of claim 1, wherein the at least one cooling assembly further includes at least one fan located inside the at least one cooling assembly, and the at least one fan is configured to regulate or accelerate a flow rate of the cooling medium flowing between the cover assembly and the at least one cooling assembly.

6. A detector module, comprising:
    a cover assembly including a chamber;
    a detector assembly including a plurality of detector components, wherein the plurality of detector components are arranged inside the chamber;
    a plurality of pipes arranged in the plurality of detector components, respectively; and
    a medium separation component operably coupled to the plurality of pipes,
    wherein
    the medium separation component includes a plurality of branch medium inlets and a plurality of branch medium outlets,
    the medium separation component is configured to distribute a cooling medium into the plurality of pipes through the plurality of branch medium inlets and the plurality of branch medium outlets, and
    each of the plurality of pipes is configured to guide a portion of the cooling medium to flow through a corresponding detector component of the plurality of detector components and cool the corresponding detector component.

7. The detector module of claim 6, wherein
    the medium separation component includes one or more medium separation sub-components;
    each of the one or more medium separation sub-components is operably coupled to at least a portion of the plurality of pipes; and
    the each of the one or more medium separation sub-components is configured to distribute a portion of the cooling medium to the one or more pipes of the plurality of pipes.

8. The detector module of claim 7, wherein
the each of the one or more medium separation sub-components includes a main medium inlet, a main medium outlet, one or more of the plurality of branch medium inlets, and one or more of the plurality of branch medium outlets; and
the cooling medium is capable of flowing from the main medium inlet to the one or more branch medium outlets or from the one or more branch medium inlets to the main medium outlet.

9. The detector module of claim 8, wherein
the each of the plurality of pipes includes an inlet port and an outlet port;
each of the one or more branch medium outlets is operably coupled to an inlet port of one of the plurality of pipes; and
each of the one or more branch medium inlets is operably coupled to an outlet port of one of the plurality of pipes.

10. The detector module of claim 8, wherein
a first branch medium outlet of the one or more branch medium outlets of the each of the one or more medium separation sub-components is closer to the main medium inlet of the each of the one or more medium separation sub-components than a second branch medium outlet of the one or more branch medium outlets; and
a first opening size of the first branch medium outlet is less than or equal to a second opening size of the second branch medium outlet.

11. The detector module of claim 7, wherein at least one of the one or more medium separation sub-components is operably coupled to one or more detector components of the plurality of detector components that are located at a central region of the detector assembly.

12. The detector module of claim 11, wherein an average flow rate of the cooling medium flowing through one or more pipes coupled to the at least one of the one or more medium separation sub-components is greater than or equal to an average flow rate of the cooling medium flowing through one or more pipes coupled to a remaining portion of the one or more medium separation sub-components.

13. The detector module of claim 7, wherein
the medium separation component includes a first medium separation sub-component, a second medium separation sub-component, and a third medium separation sub-component; and
the first medium separation sub-component, the second medium separation sub-component, and the third medium separation sub-component are independent from each other and disconnected with each other.

14. The detector module of claim 6, wherein each of the plurality of detector components includes:
an electronic component; and
a frame for supporting the electronic component, wherein the frame is equipped with a pipe of the plurality of pipes.

15. The detector module of claim 14, wherein the pipe extends along a length direction of the frame or a length direction of the electronic component.

16. The detector module of claim 6, further comprising at least one cooling assembly operably coupled to the cover assembly, wherein
each two adjacent detector components of the plurality of detector components include a gap between the each two adjacent detector components; and
the at least one cooling assembly is configured to cool the detector assembly by providing a cooling gas to the cover assembly.

17. A detector module, comprising:
a detector assembly configured to detect a signal associated with an object;
a cover assembly configured to accommodate the detector assembly;
a plurality of cooling pipes arranged in the cover assembly; and
at least one medium separation component operably coupled to the plurality of cooling pipes, wherein the at least one medium separation component includes a plurality of branch medium inlets and a plurality of branch medium outlets, and the at least one medium separation component is configured to distribute a cooling medium into the plurality of cooling pipes through the plurality of branch medium inlets and the plurality of branch medium outlets.

18. The detector module of claim 17, further including a plurality of connection pipes, wherein
the plurality of connection pipes are operably coupled to the at least one medium separation component and the plurality of cooling pipes; and
the plurality of connection pipes are configured to allow the cooling medium to flow between the plurality of cooling pipes and the medium separation component.

19. The detector module of claim 18, wherein
the plurality of connection pipes includes one or more inlet connection pipes and one or more outlet connection pipes; and
the cooling medium is capable of flowing from the at least one medium separation component, through the one or more inlet connection pipes, to the plurality of cooling pipes or from the plurality of cooling pipes, through the one or more outlet connection pipes, to the at least one medium separation component.

20. The detector module of claim 19, wherein
each of the at least one medium separation component includes a main medium inlet, a main medium outlet, one or more of the plurality of branch medium inlets, and one or more of the plurality of branch medium outlets;
the one or more inlet connection pipes are operably coupled to the one or more branch medium outlets;
the one or more outlet connection pipes are operably coupled to the one or more branch medium inlets; and
the cooling medium is capable of flowing from the main medium inlet, through the one or more branch medium outlets, into the one or more inlet connection pipes or from the one or more outlet connection pipes, through the one or more branch medium inlets, into the main medium outlet.

* * * * *